United States Patent
Hwang et al.

(10) Patent No.: US 11,473,154 B2
(45) Date of Patent: Oct. 18, 2022

(54) METHOD FOR DETECTING MUTATION IN VIRAL HEMORRHAGIC SEPTICEMIA VIRUS (VHSV) NON-VIRON (NV) GENE

(71) Applicant: REPUBLIC OF KOREA (National Institute of Fisheries Science), Busan (KR)

(72) Inventors: Jee Youn Hwang, Busan (KR); Miyoung Cho, Busan (KR); Mun Gyeong Kwon, Busan (KR); Bo-Young Jee, Busan (KR); Jung Soo Seo, Busan (KR); Seong Don Hwang, Busan (KR); Myoung Ae Park, Busan (KR); Maeng Hyun Son, Busan (KR)

(73) Assignee: NATIONAL FISHERY PRODUCTS QUALITY MANAGEMENT SERVICE, Busan (KR)

( * ) Notice: Subject to any disclaimer, the term of this patent is extended or adjusted under 35 U.S.C. 154(b) by 1163 days.

(21) Appl. No.: 15/777,659

(22) PCT Filed: May 19, 2017

(86) PCT No.: PCT/KR2017/005214
§ 371 (c)(1),
(2) Date: May 19, 2018

(87) PCT Pub. No.: WO2018/092998
PCT Pub. Date: May 24, 2018

(65) Prior Publication Data
US 2021/0164060 A1    Jun. 3, 2021

(30) Foreign Application Priority Data
Nov. 15, 2016    (KR) .......... 10-2016-0151765

(51) Int. Cl.
*C12Q 1/70*    (2006.01)
*A61K 39/00*    (2006.01)

(52) U.S. Cl.
CPC .............. *C12Q 1/701* (2013.01); *A61K 39/00* (2013.01); *C12Q 2600/156* (2013.01)

(58) Field of Classification Search
None
See application file for complete search history.

(56) References Cited

FOREIGN PATENT DOCUMENTS

| KR | 10-2014-0091944 A | 7/2014 |
|---|---|---|
| KR | 10-2015-0028063 A | 3/2015 |
| KR | 10-1595442 B1 | 2/2016 |
| KR | 1020150116166 * | 2/2016 |
| KR | 10-1642784 B1 | 7/2016 |
| KR | 10-1677012 B1 | 11/2016 |

OTHER PUBLICATIONS

Stepien et al., Research Article Gene Diversification of an Emerging Pathogen: A Decade of Mutation in a Novel Fish Viral Hemorrhagic Septicemia (VHS), 2015, PLoS ONE, pp. 1-25.*
Einer-Jensen, K., et al., "Parallel Phylogenetic Analyses Using the N, G or Nv Gene From a Fixed Group of VHSV Isolates Reveal the Same Overall Genetic Typing", "Diseases of Aquatic Organisms", 2005, pp. 39-45, vol. 67.
Hwang, J.Y., et al., "NV Gene Variation of Viral Hemorrhagic Septicemia Virus Decrease Cellular Energy Metabolism", "Aquaculture", 2016, pp. 357-363.
Petersen, K., et al., "Short PNA Molecular Beacons for Real-Time PCR Allelic Discrimination of Single Nucleotide Polymorphisms", "Molecular and Cellular Probes", 2004, pp. 117-122, vol. 18.
Schonherz, A., et al., "Ultra-Deep Sequencing of VHSV Isolates Contributes to Understanding the Role of Viral Quasispecies", "Veterinary Research", 2016, pp. 1-12, vol. 47, No. 10.
Ahn, S. J., et al., "Phylogenetic Analysis of Viral Haemorrhagic Septicaemia Virus (VHSV) Isolates from Asia", "Journal of Fish Pathology", 2013, pp. 149-161; English Abstract Only, vol. 26, No. 3.
Chinchilla, B., et al., "Transcriptome Analysis of Rainbow Trout in Response to Non-Virion (NV) Protein of Viral Haemorrhagic Septicaemia Virus (VHSV)", "Appl. Microbiol Biotechnol", 2015, pp. 1827-1843, vol. 99.
Einer-Jensen, K., et al., "High Virulence Differences Among Phylogenetically Distinct Isolates of the Fish Rhabdovirus Viral Hemmorrhagic Septicaemia Virus Are Not Explained by Variability of the Surface Glycoprotein G or the Non-Virion Protein Nv", "Journal of General Virology", 2014, pp. 307-316.

* cited by examiner

*Primary Examiner* — Benjamin P Blumel
(74) *Attorney, Agent, or Firm* — Hultquist, PLLC; Steven J. Hultquist

(57) ABSTRACT

The present invention relates to methods of identifying viral hemorrhagic septicemia virus (VHSV) and detecting mutations in VHSV by use of a PNA probe that binds specifically to VHSV non-virion gene and by analysis of the melting pattern of the PNA probe. According to the present invention, a mutation in a virus that causes infectious disease in aquatic organisms can be detected in a simple, rapid and accurate manner, infection of fish with the virus can be detected, and a mutation in the NV gene can be detected.

7 Claims, 12 Drawing Sheets
Specification includes a Sequence Listing.

Fig. 4

```
                                                                   PO-167
FOC-VHS2013-1   CAGAAATCTCCGCTACAGACTTCTTCGAGACAACTCTCTCTAGAGTCTCAGAGGATCTAA
FOC-VHS2012-6   CAGAAATCTCCGCTACAGACTTCTTCGAAACAACTC-TTCTAGAGTCTCAGAGGATCTAA
FOC-VHS2014-5   CAGAAATCTCCGCTACAGACTTCTTCGAGACAACTCTTTCTAGAGTCTCAGAGGATCTAA
FOC-VHS2013-9   CAGAAATCTCCGCTACAGACTTCTTCGAGACAACTCTTTCTAGAGTCTCAGAGGATCTAA
FOC-VHS2016-2   CAGAAATCTCCGCTACAGACTTCTTCGAGACAACTCTTTCTAGAGTCTCAGAGGATCTAA
FOC-VHS2014-4   CAGAAATCTCCGCTACAGACTTCTTCGAGACAACTCTTTCTAGAGTCTCAGAGGATCTAA
FOC-VHS2012-11  CAGAAATCTCGGATACAGACTTCTTCGAGAAAACT-TTTCTAGAGTCTCAGAGGATCTAA
FOC-VHS2014-2   CAGAAATCTCCGCTACAGACTTCTTCGAGACAACTCTTTCCAGAGTCTCAGAGGATCTAA
FOC-VHS2012-7   CAGAAATCTCCGCTACAGAATTCTTCGAGACAACTCTTTCTAGAGTCTCAGAGGATCTAA
FOC-VHS2013-2   CAGAAATCTCCGCTACAGA-TTCTTCGAGACAACTCTTTCTAGAGTCTCAGAGGATCTAA
FOC-VHS2013-4   CAGAAATCCGCTACAGAA-TTCTTCGAGACAACTCTTTCTAGAGTCTCAGAGGATCTAA
FOC-VHS2013-3   CAGAAATCTCCGCTACAGACTTCTTCGAGACAACTCTTTCTAGAGTCTTAGAGGATCTAA
FOC-VHS2012-9   CAGAAATCTCCGCTACAGACTTCTTCGAGAGAACTCTCTATAGAGTCTCAGAGGATCTAA
FOC-VHS2012-10  CAGAAATCTCCGCTACAGACTTCTTCGAGACAACT-TTTCTAGAGTCTCAGAGGATCTAA
FOC-VHS2016-1   CAGAAATCTCCGCTACAGACTTCTTCGAGACAACT-TTTCTAGAGTCTCAGAGGATCTAA
                *******  *        *  ********  *  ****    *  *******  ****** ***
```

Fig. 5

```
                                                              PO-350
FOC-VHS2013-1   ATCCTGGACTCTTCATCATTTCACTTGAGGGAATGAAGACCTTGACGAATGGTCGAAAT
FOC-VHS2012-6   ATCCTGGACTCTTCATCATTTCACTTGAGGGAATGAAAACCTTGACGAATGGTCGGAAT
FOC-VHS2014-5   ATCCTGGACTCTTCATCATTTCACTTGAGGGAATGAAAACCTTGACGAATGGTCGGAAT
FOC-VHS2013-9   ATCCTGGACTCTTCATCATTTCACTTGAGGGAATGAAAACCTTGACGAATGGTCGGAAT
FOC-VHS2016-2   ATCCTGGACTCTTCATCATTTCACTTGAGGGAATGAAAACCTTGACGAATGGTCGGAAT
FOC-VHS2014-4   ATCCTGGACTCTTCATCATTTCACTTGAGGGAATGAAAACCTTGACGAATGGTCGGAAT
FOC-VHS2012-11  ATCCTGGACTCTTCATCATTTCACTTGAGGGAATGAAAACCTTGACGAATGGTCGGAAT
FOC-VHS2014-2   ATCCTGGACTCTTCATCATTTCACTTGAGGGAATGAAAACCTTGACGAATGGTCGGAGT
FOC-VHS2012-7   ATCCTGGACTCTTCATCATTTCACTTGAGGGAATGAAAACCTTAACGAATGGTCGGAAT
FOC-VHS2013-2   ATCCTGGACTCTTCATCATTTCACTTGAGGGAATGAAAACCTTGACGAATGGTCGGAAT
FOC-VHS2013-4   ATCCTGGACTCTTCATCATTTCACTTGAGGGAATGAAAACCTTGACGAATGGTCGGAAT
FOC-VHS2013-3   ATCCTGGACTCTTCATCATTTCACTTGAGGGAATGAAAACCTTGACGAATGACTCGGAAT
FOC-VHS2012-9   ATCCTGGACTCTTCATCATTTCACTTGAGGGAATGAAAACCTTGACGAATGGTCGGAAT
FOC-VHS2012-10  ATCCTGGACTCTTCATCATTTCACTTGAGGGAATGAAAACCTTGACGAATGGTCGGAAT
FOC-VHS2016-1   ATCCTGGACTCTTCATCATTTCACTTGAGGGAATGAAAACCTTGACGAATGGTCGGAAT
                ****************************************  *****  *******  ****  *  *
```

Fig. 6

```
                                           PO-241           PO-262
FOC-VHS2013-1   ACATGAGGATAAGTCTCCTAGAGGGAGCTCATTACAGTAAGGAATGTCGCCTCCAGTCCT
FOC-VHS2012-6   ACATGAGGATAAGTCTTCTAGAGGGAACTCATTACATTAAGGAATGTCCCCTCCAGTCCT
FOC-VHS2014-5   ACATGAGGATAAGTCTTCTAGAGGGAACTCATTACATTAAGGAATATCCCCTCCAGTCCT
FOC-VHS2013-9   ACATGAGGATAAGTCTTCTAGAGGGAACTCATTACATTAAGGAATGTCCCCTCCAGTCCT
FOC-VHS2016-2   ACATGAGGATAAGTCTTCTAGAGGGAACTCATTACATTAAGGAATGTCCCCTCCAGTCCT
FOC-VHS2014-4   ACATGAGGATAAGTCTTCTAGAGGGAACCATTACATTAAGGAATGTCCCCTCCAGTCCT
FOC-VHS2012-11  ACATGAGGATAAGTCTTCTAGAGGGAACTCATTACATTAAGGAATGTCCCCTCCAGTCCT
FOC-VHS2014-2   ACATGAGGATAAGTCTTCTAGAGGGAACTCATTACAGTAAGGAATGTCCCCTCCAGTCCT
FOC-VHS2012-7   ACATGAGGATAAGTCTTCTAGAGGGAACTCATTACATTAAGGAATGTCCCCTCCAGTCCT
FOC-VHS2013-2   ACATGAGGATAAGTCTTCTAGAGGGAACTCATTACATTAAGGAATGTCCCCTCCAGTCCT
FOC-VHS2013-4   ACATGAGGATAAGTCTTCTAGAGGGAACTCATTACATTAAGGAATGTCCCCTCCAGTCCT
FOC-VHS2013-3   ACATGAGGATAAGTCTTCTAGAGGGAACTCATTACATTAAGGAATGTCCCCTCCAGTCCT
FOC-VHS2012-9   ACATGAGGATAAGTCTTCTAGAGGGAACTCATTACATTAAGGAATGTCCCCTCCAGTCCT
FOC-VHS2012-10  ACATGAGGATAAGTCTTCTAGAGGGAACTCATTACATTAAGGAATGTCCCCTCCAGTCCT
FOC-VHS2016-1   ACATGAGGATAAGTCTTCTAGAGGGAACTCATTACATTAAGGAATGTCCCCTCCAGTCCT
                **************** *******  *  *******  *******  ***************
```

Analysis of melting temperatures of 15 VHSV samples

|  |  | Set 1 | | | Set 2 | | |
|---|---|---|---|---|---|---|---|
| No. | Sample | PO-241(°C) | PO-167(°C) | PO-355(°C) | PO-350(°C) | PO-262(°C) | PO-23(°C) |
| 1 | FDC-VHS2012-10 | 65 | 64 | 50 | 58 | 58 | 65 |
| 2 | FDC-VHS2012-6 | 66 | 64 | 50 | 58 | 58 | 65 |
| 3 | FDC-VHS2012-7 | 65 | 64 | 50 | 58 | 60 | 65 |
| 4 | FDC-VHS2012-9 | 66 | 64 | 50 | 58 | 58 | 66 |
| 5 | FDC-VHS2012-11 | 65 | 64 | 50 | 58 | 60 | 65 |
| 6 | FDC-VHS2013-2 | 65 | 64 | 50 | 58 | 58 | 65 |
| 7 | FDC-VHS2013-4 | 65 | 64 | 50 | 58 | 58 | 65 |
| 8 | FDC-VHS2013-3 | 65 | 45 | 50 | 47 | 58 | 65 |
| 9 | FDC-VHS2013-9 | 65 | 64 | 50 | 58 | 58 | 55 |
| 10 | FDC-VHS2014-5 | 65 | 64 | 50 | 58 | 49 | 66 |
| 11 | FDC-VHS2014-4 | 58 | 64 | 50 | 58 | 58 | 55 |
| 12 | FDC-VHS2014-2 | 65 | 64 | - | 58 | 60 | 66 |
| 13 | FDC-VHS2013-1 | 47 | 63 | 61 | 58 | 60 | 65 |
| 14 | FDC-VHS2016-1 | 65 | 64 | 50 | 58 | 58 | 66 |
| 15 | FDC-VHS2016-2 | 65 | 64 | 50 | 58 | 58 | 56 |

Relationship between the melting temperatures of PNA probes included in set 1 and the nucleotide sequences Set 1

| No. | Sample | PO-262 Sequence | Tm (°C) | PO-350 Sequence | Tm (°C) | PO-355 Sequence | Tm (°C) |
|---|---|---|---|---|---|---|---|
| 1 | FDC-VHS2012-10 | TTAAGGAATGTCCC | 58 | ACGAATGGCTCC | 58 | CTCCGAATCTCCCC | 50 |
| 2 | FDC-VHS2012-6 | TTAAGGAATGTCCC | 58 | ACGAATGGCTCC | 58 | CTCCGAATCTCCCC | 50 |
| 3 | FDC-VHS2012-7 | CTAAGGAATGTCCC | 60 | ACGAATGGCTCC | 58 | CTCCGAATCTCCCC | 50 |
| 4 | FDC-VHS2012-9 | TTAAGGAATGTCCC | 58 | ACGAATGGCTCC | 58 | CTCCGAATCTCCCC | 50 |
| 5 | FDC-VHS2012-11 | CTAAGGAATGTCCC | 60 | ACGAATGGCTCC | 58 | CTCCGAATCTCCCC | 50 |
| 6 | FDC-VHS2013-2 | TTAAGGAATGTCCC | 58 | ACGAATGGCTCC | 58 | CTCCGAATCTCCCC | 50 |
| 7 | FDC-VHS2013-4 | TTAAGGAATGTCCC | 58 | ACGAATGACTCC | 47 | CTCCGAATCTCCCC | 50 |
| 8 | FDC-VHS2013-3 | TTAAGGAATGTCCC | 58 | ACGAATGGCTCC | 58 | CTCCGAATCTCCCC | 50 |
| 9 | FDC-VHS2013-9 | TTAAGGAATGTCCC | 58 | ACGAATGGCTCC | 58 | CTCCGAATCTCCCC | 50 |
| 10 | FDC-VHS2014-5 | TTAAGGAATATCCC | 49 | ACGAATGGCTCC | 58 | CTCCGAATCTCCCC | 50 |
| 11 | FDC-VHS2014-4 | TTAAGGAATGTCCC | 58 | ACGAATGGCTCC | 58 | CTCCGAATCTCCCC | 50 |
| 12 | FDC-VHS2014-2 | CTAAGGAATGTCCC | 60 | ACGAATGGCTCC | 58 | CTCCGASTCTCCCC | - |
| 13 | FDC-VHS2013-1 | CTAAGGAATGTCCC | 60 | ACGAATGGCTCC | 58 | CTCCXAATCTCCCC | 61 |
| 14 | FDC-VHS2016-1 | TTAAGGAATGTCCC | 58 | ACGAATGGCTCC | 58 | CTCCGAATCTCCCC | 50 |
| 15 | FDC-VHS2016-2 | TTAAGGAATGTCCC | 58 | ACGAATGGCTCC | 58 | CTCCGAATCTCCCC | 50 |

Fig. 16

Relationship between the melting temperatures of PNA probes included in set 2 and the nucleotide sequences
Set 2

| No. | Sample | PO-23 Sequence | Tm (°C) | PO-167 Sequence | Tm (°C) | PO-241 Sequence | Tm (°C) |
|---|---|---|---|---|---|---|---|
| 1 | FDC-VHS2012-10 | ACACAGCACAACC | 65 | AGTCTCAGAGGATC | 64 | AGAGGGAACTCAT | 65 |
| 2 | FDC-VHS2012-6 | ACACAGCACAACC | 65 | AGTCTCAGAGGATC | 64 | AGAGGGAACTCAT | 66 |
| 3 | FDC-VHS2012-7 | ACACAGCACAACC | 65 | AGTCTCAGAGGATC | 64 | AGAGGGAACTCAT | 65 |
| 4 | FDC-VHS2012-9 | ACACAGCACAACC | 66 | AGTCTCAGAGGATC | 64 | AGAGGGAACTCAT | 66 |
| 5 | FDC-VHS2012-11 | ACACAGCACAACC | 65 | AGTCTCAGAGGATC | 64 | AGAGGGAACTCAT | 65 |
| 6 | FDC-VHS2013-2 | ACACAGCACAACC | 65 | AGTCTCAGAGGATC | 64 | AGAGGGAACTCAT | 65 |
| 7 | FDC-VHS2013-4 | ACACAGCACAACC | 65 | AGTCTCAGAGGATC | 64 | AGAGGGAACTCAT | 65 |
| 8 | FDC-VHS2013-3 | ACACAGCACAACC | 65 | AGTCTTAGAGGATC | 45 | AGAGGGAACTCAT | 65 |
| 9 | FDC-VHS2013-9 | ACACAACACAACC | 55 | AGTCTCAGAGGATC | 64 | AGAGGGAACTCAT | 65 |
| 10 | FDC-VHS2014-5 | ACACAGCACAACC | 66 | AGTCTCAGAGGATC | 64 | AGAGGGAACTCAT | 65 |
| 11 | FDC-VHS2014-4 | ACACAACACAACC | 55 | AGTCTCAGAGGATC | 64 | AGAGGGAACCCAT | 58 |
| 12 | FDC-VHS2014-2 | ACACAGCACAACC | 66 | AGTCTCAGAGGATC | 64 | AGAGGGAACTCAT | 65 |
| 13 | FDC-VHS2013-1 | ACACAGCACAACC | 65 | AGTCTCAGAGGATC | 63 | AGAGGGAGCTCAT | 47 |
| 14 | FDC-VHS2016-1 | ACACAGCACAACC | 66 | AGTCTCAGAGGATC | 64 | AGAGGGAACTCAT | 65 |
| 15 | FDC-VHS2016-2 | ACACAGCACAACC | - (66?) | AGTCTCAGAGGATC | 64 | AGAGGGAACTCAT | 65 |

Fig. 17

Conversion of melting temperature values of PNA probes into barcodes by use of judgment table

| No. | Sample | Set 1 | | | | | Set 2 | | | Barcode |
|---|---|---|---|---|---|---|---|---|---|---|
| | | PO-241(°C) | PO-161(°C) | PO-355(°C) | PO-350(°C) | | PO-262(°C) | PO-23(°C) | |
| 1 | FDC-VHS2012-10 | 1 | 1 | 2 | 1 | | 2 | 1 | 112121 |
| 2 | FDC-VHS2012-6 | 1 | 1 | 2 | 1 | | 2 | 1 | 112121 |
| 3 | FDC-VHS2012-7 | 1 | 1 | 2 | 1 | | 1 | 1 | 112111 |
| 4 | FDC-VHS2012-9 | 1 | 1 | 2 | 1 | | 2 | 1 | 112121 |
| 5 | FDC-VHS2012-11 | 1 | 1 | 2 | 1 | | 1 | 1 | 112111 |
| 6 | FDC-VHS2013-2 | 1 | 1 | 2 | 1 | | 2 | 1 | 112121 |
| 7 | FDC-VHS2013-4 | 1 | 2 | 2 | 1 | | 2 | 1 | 112121 |
| 8 | FDC-VHS2013-3 | 1 | 1 | 2 | 2 | | 2 | 1 | 122221 |
| 9 | FDC-VHS2013-9 | 1 | 1 | 2 | 1 | | 2 | 2 | 112122 |
| 10 | FDC-VHS2014-5 | 1 | 1 | 2 | 1 | | 3 | 1 | 112131 |
| 11 | FDC-VHS2014-4 | 2 | 1 | 2 | 1 | | 2 | 2 | 212112 |
| 12 | FDC-VHS2014-2 | 1 | 1 | 3 | 1 | | 1 | 1 | 113111 |
| 13 | FDC-VHS2013-1 | 3 | 1 | 1 | 1 | | 1 | 1 | 111111 |
| 14 | FDC-VHS2016-1 | 1 | 1 | 2 | 1 | | 2 | 1 | 112121 |
| 15 | FDC-VHS2016-2 | 1 | 1 | 2 | 1 | | 2 | 2 | 112122 |

Detection of mutations by data indicated by barcodes

| No. | Sample | Barcode | Diagnosis of mutation |
|---|---|---|---|
| 1 | FDC-VHS2012-10 | 112121 | 253 C>T |
| 2 | FDC-VHS2012-6 | 112121 | 253 C>T |
| 3 | FDC-VHS2012-7 | 112111 | Normal (no mutation) |
| 4 | FDC-VHS2012-9 | 112121 | 253 C>T |
| 5 | FDC-VHS2012-11 | 112111 | Normal (no mutation) |
| 6 | FDC-VHS2013-2 | 112121 | 253 C>T |
| 7 | FDC-VHS2013-4 | 112121 | 253 C>T |
| 8 | FDC-VHS2013-3 | 122221 | 167 C>T, 350 G>A, 253 C>T |
| 9 | FDC-VHS2013-9 | 112122 | 23 G>A, 253 C>T |
| 10 | FDC-VHS2014-5 | 112131 | 253 C>T, 262 C>A |
| 11 | FDC-VHS2014-4 | 212112 | 23 G>A, 243 C>T, 253 C>T |
| 12 | FDC-VHS2014-2 | 113111 | 357 A>G |
| 13 | FDC-VHS2013-1 | 111111 | 241 A>G, 355 G>A |
| 14 | FDC-VHS2016-1 | 112121 | 253 C>T |
| 15 | FDC-VHS2016-2 | 112122 | 23 G>A, 253 C>T |

SEQUENCE LISTING

```
<160> NUMBER OF SEQ ID NOS: 41

<210> SEQ ID NO 1
<211> LENGTH: 13
<212> TYPE: DNA
<213> ORGANISM: Artificial Sequence
<220> FEATURE:
<223> OTHER INFORMATION: PNA Probe PO-23

<400> SEQUENCE: 1
acacagcaca acc                                                        13

<210> SEQ ID NO 2
<211> LENGTH: 14
<212> TYPE: DNA
<213> ORGANISM: Artificial Sequence
<220> FEATURE:
<223> OTHER INFORMATION: PNA Probe PO-167

<400> SEQUENCE: 2
agtctcagag gatc                                                       14

<210> SEQ ID NO 3
```

```
<211> LENGTH: 13
<212> TYPE: DNA
<213> ORGANISM: Artificial Sequence
<220> FEATURE:
<223> OTHER INFORMATION: PNA Probe PO-241

<400> SEQUENCE: 3
agagggaact cat                                                      13

<210> SEQ ID NO 4
<211> LENGTH: 14
<212> TYPE: DNA
<213> ORGANISM: Artificial Sequence
<220> FEATURE:
<223> OTHER INFORMATION: PNA Probe PO-262

<400> SEQUENCE: 4
ctaaggaatg tccc                                                     14

<210> SEQ ID NO 5
<211> LENGTH: 12
<212> TYPE: DNA
<213> ORGANISM: Artificial Sequence
<220> FEATURE:
<223> OTHER INFORMATION: PNA Probe PO-350

<400> SEQUENCE: 5
acgaatggct cc                                                       12

<210> SEQ ID NO 6
<211> LENGTH: 14
<212> TYPE: DNA
<213> ORGANISM: Artificial Sequence
<220> FEATURE:
<223> OTHER INFORMATION: PNA Probe PO-355

<400> SEQUENCE: 6
ctccaaatct cccc                                                     14

<210> SEQ ID NO 7
<211> LENGTH: 19
<212> TYPE: DNA
<213> ORGANISM: Artificial Sequence
<220> FEATURE:
<223> OTHER INFORMATION: primer

<400> SEQUENCE: 7
aaaatggcac ccctgtgag                                                19

<210> SEQ ID NO 8
<211> LENGTH: 18
<212> TYPE: DNA
<213> ORGANISM: Artificial Sequence
<220> FEATURE:
<223> OTHER INFORMATION: primer

<400> SEQUENCE: 8
gtattacccc ctgtaggg                                                 18

<210> SEQ ID NO 9
<211> LENGTH: 60
<212> TYPE: DNA
<213> ORGANISM: Artificial Sequence
<220> FEATURE:
<223> OTHER INFORMATION: Synthetic construct

<400> SEQUENCE: 9
```
agatgacgac ccagtcggca cacagcacaa ccagcttctc tccacttgtc cttcgtgaga      60

<210> SEQ ID NO 10
<211> LENGTH: 60
<212> TYPE: DNA
<213> ORGANISM: Artificial Sequence
<220> FEATURE:
<223> OTHER INFORMATION: Synthetic construct

<400> SEQUENCE: 10
agatgacgac ccagtcggca cacagcacaa ccagcttctc tccacttgtc cttcgcgaga      60

<210> SEQ ID NO 11
<211> LENGTH: 60
<212> TYPE: DNA
<213> ORGANISM: Artificial Sequence
<220> FEATURE:
<223> OTHER INFORMATION: Synthetic construct

<400> SEQUENCE: 11
agatgacgac ccagtcggca cacaacacaa ccagcttctc tccacttgtc cttcgcgaga      60

<210> SEQ ID NO 12
<211> LENGTH: 60
<212> TYPE: DNA
<213> ORGANISM: Artificial Sequence
<220> FEATURE:
<223> OTHER INFORMATION: Synthetic construct

<400> SEQUENCE: 12
agatgacgac tcagtcggca cacagcacaa ccagcttctc tccacttgtc cttcgcgaga      60

<210> SEQ ID NO 13
<211> LENGTH: 60
<212> TYPE: DNA
<213> ORGANISM: Artificial Sequence
<220> FEATURE:
<223> OTHER INFORMATION: Synthetic construct

<400> SEQUENCE: 13
cagaaatctc cgctacagac ttcttcgaga caactctctc tagagtctca gaggatctaa      60

<210> SEQ ID NO 14
<211> LENGTH: 59
<212> TYPE: DNA
<213> ORGANISM: Artificial Sequence
<220> FEATURE:
<223> OTHER INFORMATION: Synthetic construct

<400> SEQUENCE: 14
cagaaatctc cgctacagac ttcttcgaaa caactcttct agagtctcag aggatctaa       59

<210> SEQ ID NO 15
<211> LENGTH: 60
<212> TYPE: DNA
<213> ORGANISM: Artificial Sequence
<220> FEATURE:
<223> OTHER INFORMATION: Synthetic construct

<400> SEQUENCE: 15
cagaaatctc cgctacagac ttcttcgaga caactctttc tagagtctca gaggatctaa      60

<210> SEQ ID NO 16
<211> LENGTH: 59
<212> TYPE: DNA

<210> SEQ ID NO 17
<211> LENGTH: 60
<212> TYPE: DNA
<213> ORGANISM: Artificial Sequence
<220> FEATURE:
<223> OTHER INFORMATION: Synthetic construct

<400> SEQUENCE: 16
cagaaatctc cgatacagac ttcttcgaga aaactttct agagtctcag aggatctaa    59

<210> SEQ ID NO 17
<211> LENGTH: 60
<212> TYPE: DNA
<213> ORGANISM: Artificial Sequence
<220> FEATURE:
<223> OTHER INFORMATION: Synthetic construct

<400> SEQUENCE: 17
cagaaatctc cgctacagac ttcttcgaga caactctttc cagagtctca gaggatctaa    60

<210> SEQ ID NO 18
<211> LENGTH: 60
<212> TYPE: DNA
<213> ORGANISM: Artificial Sequence
<220> FEATURE:
<223> OTHER INFORMATION: Synthetic construct

<400> SEQUENCE: 18
cagaaatctc cgctacagaa ttcttcgaga caactctttc tagagtctca gaggatctaa    60

<210> SEQ ID NO 19
<211> LENGTH: 59
<212> TYPE: DNA
<213> ORGANISM: Artificial Sequence
<220> FEATURE:
<223> OTHER INFORMATION: Synthetic construct

<400> SEQUENCE: 19
cagaaatctc cgctacagat tcttcgagac aactctttct agagtctcag aggatctaa    59

<210> SEQ ID NO 20
<211> LENGTH: 59
<212> TYPE: DNA
<213> ORGANISM: Artificial Sequence
<220> FEATURE:
<223> OTHER INFORMATION: Synthetic construct

<400> SEQUENCE: 20
cagaaattcc gctacagaat tcttcgagac aactctttct agagtctcag aggatctaa    59

<210> SEQ ID NO 21
<211> LENGTH: 60
<212> TYPE: DNA
<213> ORGANISM: Artificial Sequence
<220> FEATURE:
<223> OTHER INFORMATION: Synthetic construct

<400> SEQUENCE: 21
cagaaatctc cgctacagac ttcttcgaga caactctttc tagagtctta gaggatctaa    60

<210> SEQ ID NO 22
<211> LENGTH: 60
<212> TYPE: DNA
<213> ORGANISM: Artificial Sequence
<220> FEATURE:
<223> OTHER INFORMATION: Synthetic construct

<400> SEQUENCE: 22
cagaaatctc cgctacagac ttcttcgaga caactctcta tagagtctca gaggatctaa    60

<210> SEQ ID NO 23
<211> LENGTH: 59
<212> TYPE: DNA
<213> ORGANISM: Artificial Sequence
<220> FEATURE:
<223> OTHER INFORMATION: Synthetic construct

<400> SEQUENCE: 23
cagaaatctc cgctacagac ttcttcgaga caactttct agagtctcag aggatctaa      59

<210> SEQ ID NO 24
<211> LENGTH: 60
<212> TYPE: DNA
<213> ORGANISM: Artificial Sequence
<220> FEATURE:
<223> OTHER INFORMATION: Synthetic construct

<400> SEQUENCE: 24
atcctggact cttcatcatt tcacttgagg gaatgaagac cttgacgaat ggctccaaat     60

<210> SEQ ID NO 25
<211> LENGTH: 60
<212> TYPE: DNA
<213> ORGANISM: Artificial Sequence
<220> FEATURE:
<223> OTHER INFORMATION: Synthetic construct

<400> SEQUENCE: 25
atcctggact cttcatcatt tcacttgagg gaatgaaaac cttgacgaat ggctccgaat     60

<210> SEQ ID NO 26
<211> LENGTH: 60
<212> TYPE: DNA
<213> ORGANISM: Artificial Sequence
<220> FEATURE:
<223> OTHER INFORMATION: Synthetic construct

<400> SEQUENCE: 26
atcctggact cttcatcatt tcacttgagg gaatgaaaac cttgacgaat ggctccgagt     60

<210> SEQ ID NO 27
<211> LENGTH: 60
<212> TYPE: DNA
<213> ORGANISM: Artificial Sequence
<220> FEATURE:
<223> OTHER INFORMATION: Synthetic construct

<400> SEQUENCE: 27
atcctggact cttcatcatt tcacttgagg gaatgaaaac cttaacgaat ggctccgaat     60

<210> SEQ ID NO 28
<211> LENGTH: 60
<212> TYPE: DNA
<213> ORGANISM: Artificial Sequence
<220> FEATURE:
<223> OTHER INFORMATION: Synthetic construct

<400> SEQUENCE: 28
atcctggact cttcatcatt tcacttgagg gaatgaaaac cttgacgaat gactccgaat     60

<210> SEQ ID NO 29
<211> LENGTH: 60
<212> TYPE: DNA
<213> ORGANISM: Artificial Sequence
<220> FEATURE:

<223> OTHER INFORMATION: Synthetic construct

<400> SEQUENCE: 29
acatgaggat aagtctccta gagggagctc attacactaa ggaatgtccc ctccagtcct    60

<210> SEQ ID NO 30
<211> LENGTH: 60
<212> TYPE: DNA
<213> ORGANISM: Artificial Sequence
<220> FEATURE:
<223> OTHER INFORMATION: Synthetic construct

<400> SEQUENCE: 30
acatgaggat aagtcttcta gagggaactc attacattaa ggaatgtccc ctccagtcct    60

<210> SEQ ID NO 31
<211> LENGTH: 60
<212> TYPE: DNA
<213> ORGANISM: Artificial Sequence
<220> FEATURE:
<223> OTHER INFORMATION: Synthetic construct

<400> SEQUENCE: 31
acatgaggat aagtcttcta gagggaactc attacattaa ggaatatccc ctccagtcct    60

<210> SEQ ID NO 32
<211> LENGTH: 60
<212> TYPE: DNA
<213> ORGANISM: Artificial Sequence
<220> FEATURE:
<223> OTHER INFORMATION: Synthetic construct

<400> SEQUENCE: 32
acatgaggat aagtcttcta gagggaactc attacattaa ggaatgtccc ctccagtcct    60

<210> SEQ ID NO 33
<211> LENGTH: 60
<212> TYPE: DNA
<213> ORGANISM: Artificial Sequence
<220> FEATURE:
<223> OTHER INFORMATION: Synthetic construct

<400> SEQUENCE: 33
acatgaggat aagtcttcta gagggaaccc attacattaa ggaatgtccc ctccagtcct    60

<210> SEQ ID NO 34
<211> LENGTH: 60
<212> TYPE: DNA
<213> ORGANISM: Artificial Sequence
<220> FEATURE:
<223> OTHER INFORMATION: Synthetic construct

<400> SEQUENCE: 34
acatgaggat aagtcttcta gagggaactc attacactaa ggaatgtccc ctccagtcct    60

<210> SEQ ID NO 35
<211> LENGTH: 59
<212> TYPE: DNA
<213> ORGANISM: Artificial Sequence
<220> FEATURE:
<223> OTHER INFORMATION: Synthetic construct

<400> SEQUENCE: 35
acatgaggat aagtcttcta gagggaactc atacattaag gaatgtcccc tccagtcct    59

```
<210> SEQ ID NO 36
<211> LENGTH: 60
<212> TYPE: DNA
<213> ORGANISM: Artificial Sequence
<220> FEATURE:
<223> OTHER INFORMATION: Synthetic construct

<400> SEQUENCE: 36
gaatggctcc aaatctcccc catgaactcc ttccccttct cccagataga aaaaaatggc    60

<210> SEQ ID NO 37
<211> LENGTH: 60
<212> TYPE: DNA
<213> ORGANISM: Artificial Sequence
<220> FEATURE:
<223> OTHER INFORMATION: Synthetic construct

<400> SEQUENCE: 37
gaatggctcc gaatctcccc catgaactcc tccccttct cccagataga aaaaaatggc     60

<210> SEQ ID NO 38
<211> LENGTH: 60
<212> TYPE: DNA
<213> ORGANISM: Artificial Sequence
<220> FEATURE:
<223> OTHER INFORMATION: Synthetic construct

<400> SEQUENCE: 38
gaatggctcc gagtctcccc catgaactcc tccccttct cccagataga aaaaaatggc     60

<210> SEQ ID NO 39
<211> LENGTH: 60
<212> TYPE: DNA
<213> ORGANISM: Artificial Sequence
<220> FEATURE:
<223> OTHER INFORMATION: Synthetic construct

<400> SEQUENCE: 39
gaatggctcc gaatctcccc catgaactcc tcctccttct cccagataga aaaaaatggc    60

<210> SEQ ID NO 40
<211> LENGTH: 60
<212> TYPE: DNA
<213> ORGANISM: Artificial Sequence
<220> FEATURE:
<223> OTHER INFORMATION: Synthetic construct

<400> SEQUENCE: 40
gaatgactcc gaatctcccc catgaactcc tccccttct cccagataga aaaaaatggc     60

<210> SEQ ID NO 41
<211> LENGTH: 60
<212> TYPE: DNA
<213> ORGANISM: Artificial Sequence
<220> FEATURE:
<223> OTHER INFORMATION: Synthetic construct

<400> SEQUENCE: 41
gaatggctcc gaatctcccc catgaactcc tcccccctct cccagataga aaaaaatggc    60
```

…

METHOD FOR DETECTING MUTATION IN VIRAL HEMORRHAGIC SEPTICEMIA VIRUS (VHSV) NON-VIRON (NV) GENE

CROSS-REFERENCE TO RELATED APPLICATIONS

This application is a U.S. national phase under the provisions of 35 U.S.C. § 371 of International Patent Application No. PCT/KR17/05214 filed May 19, 2017, which in turn claims priority of Korean Patent Application No. 10-2016-0151765 filed Nov. 15, 2016. The disclosures of such international patent application and Korean priority patent application are hereby incorporated herein by reference in their respective entireties, for all purposes.

REFERENCE TO SEQUENCE LISTING SUBMITTED VIA EFS-WEB

This application includes an electronically submitted sequence listing in .txt format. The .txt file contains a sequence listing entitled "425_UpdatedSeqListing_ST25.txt" created on Jun. 17, 2022 and is 8,240 bytes in size. The sequence listing contained in this .txt file is part of the specification and is hereby incorporated by reference herein in its entirety.

TECHNICAL FIELD

The present invention relates to a method for detecting a mutation in viral hemorrhagic septicemia virus (VHSV) non-virion (NV) gene, and more particularly to a PNA probe that binds specifically to a specific gene of VHSV and a method of detecting a mutation in VHSV NV gene by analysis of the melting pattern of the PNA probe.

BACKGROUND ART

Viral hemorrhagic septicemia virus (VHSV) is a virus that causes viral hemorrhagic septicemia (VHS) in fish. VHSV infection is associated with factors, including the kind of fish, the size of the fish body, and water temperature, and is characterized by horizontal transmission from fish to fish and vertical transmission from mother to eggs.

The optimum water temperature at which fish of the family Salmonidae is infected with VHSV to display disease is about 8° C., and Korean flatfish is infected with VHSV at a temperature of 20° C.~15° C. or below. VHSV infection of Korean flatfish occurs mainly during the low water temperature period from autumn to the next spring to cause great damage to the fishery industry.

It was reported that VHSV causes damage to Korean aquacultured flatfishes during the low water temperature period from winter to spring in 2001. Since 2001, symptoms of VHSV infection have been observed during a similar period annually. Thus, VHSV infection has been classified as a general viral disease. Viral diseases that affect Korean flatfish include VHSV, Hirame rhabdovirus (HIRRV), Aquabirnavirus, and the like. Among these viral diseases, VHSV causes the greatest damage to Korean flatfish. Furthermore, VHS is one of legal communicable diseases provided in the Aquatic Life Disease Control Act.

Among six viral proteins that are produced by VHSV, the NV region is the only non-structural protein that is distributed mainly in the cytoplasm of flatfish cells. Several previous studies revealed that the NV protein functions as a pathogenic protein that shows VHS pathology.

Meanwhile, typical methods for mutation detection include various analysis techniques, including a sequencing technique, a polymerase chain reaction (PCR) technique and a microarray technique. In a prior art gene sequencing method, according to the principle of a gene amplification technique (PCR), dNTP and a small amount of ddNTP are added, and DNA chains having different lengths are polymerized while ddNTP binds randomly, and the DNA chains are aligned according to their length while they are separated by electrophoresis. However, at present, four different fluorescent dyes are attached to each ddNTP, and when the ddNTP binds, information of each nucleotide sequence can be confirmed using a fluorescent detector. This sequencing method has very high accuracy, but requires a considerable amount of time for sequencing, and external conditions, including mixing of a sample and the concentration of a sample, serve as a disadvantage in analysis of results. Particularly, temporal consumption can be a very important variable in case of emergency. For example, in the case of RNA viruses in which genetic mutations frequently occur, the genetic mutations should be rapidly predicted so that spreading of the RNA virus can be prevented in the early stages. However, the prior art techniques entail a problem in that such mutations are not rapidly detected.

In the meantime, in recent years, analysis of not the whole gene nucleotide sequence but a specific region or marker in place of the whole gene nucleotide sequence has been actively applied. Particularly, methods capable of easily detecting genetic mutations using probes have been developed and used. However, conventional hydrolysis probe methods have a technical limitation in that it can detect only a region or marker having genetic information. In addition, technical limitations of conventional probe methods are as follows. First, it is required to know information about the nucleotide sequence to be constructed. Second, when a change in the nucleotides of a constructed probe region occurs, the result cannot be confirmed so that the result cannot be derived. Finally, the gene product to be detected should be constructed to have a length of less than 100 bp to 200 bp so that it is low-coverage verification for a previously known nucleotide sequence. Consequently, conventional probe methods excluding sequencing systems have a problem in that these methods do not analyze gene nucleotide sequences, but can perform only low-coverage verification (presence or absence of a region or a marker) for a previously known nucleotide sequence.

Accordingly, the present inventors have made extensive efforts to efficiently detect a mutation in the non-viron (NV) gene of viral hemorrhagic septicemia virus (VHSV) that causes an infectious disease in aquatic organisms, and as a result, have found that when the melting pattern of a probe having attached thereto a reporter and a quencher is compared with the melting pattern of samples, the nucleotide sequence identity between samples, the presence or absence of a nucleotide sequence mutation, and the position of a nucleotide sequence mutation can be determined in a rapid and accurate manner, thereby completing the present invention.

DISCLOSURE OF INVENTION

Technical Problem

An object of the present invention is to provide a method of detecting a mutation in viral hemorrhagic septicemia virus (VHSV) non-viron (NV) gene by use of a PNA probe having attached thereto a reporter and a quencher.

Another object of the present invention is to provide a kit for confirming the position of a nucleotide sequence mutation in viral hemorrhagic septicemia virus (VHSV) non-viron (NV) gene, the kit comprising the above-described PNA probe.

Technical Solution

To achieve the above object, the present invention provides a method of determining a mutation in viral hemorrhagic septicemia virus (VHSV) non-viron (NV) gene by use of a PNA probe having attached thereto a reporter and a quencher, the method comprising the steps of:

(a) hybridizing the PNA probe to the sample by mixing (i) a sample containing either viral hemorrhagic septicemia virus (VHSV) or a target nucleic acid comprising a mutation site of the viral hemorrhagic septicemia virus (VHSV) non-viron (NV) gene, and (ii) a PNA probe that binds complementarily to the nucleotide sequence of the target nucleic acid comprising the mutation site of the viral hemorrhagic septicemia virus (VHSV) NV gene;

(b) obtaining a melting temperature of the hybridization product while changing the temperature of the hybridization product;

(c) assigning a code after sectionalizing the melting temperature of the hybridization product; and (d) reacting a sample expected to have mutation under the same conditions as steps (a) to (b) to thereby obtain the melting temperature of the sample, and encoding the obtained melting temperature referring to the assigned code of step (c), thereby determining the type of the mutation in viral hemorrhagic septicemia virus (VHSV) non-viron (NV) gene.

The present invention also provides a kit for confirming the position of a nucleotide sequence mutation in viral hemorrhagic septicemia virus (VHSV) non-viron (NV) gene, the kit comprising a plurality of PNA probes, each of which has a reporter and or a quencher attached thereto, binds complementarily to the viral hemorrhagic septicemia virus (VHSV) non-viron (NV) gene, and has a nucleotide sequence selected from SEQ ID NOs: 1 to 6.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 2 is a schematic view showing a step of hybridizing and a step of obtaining a melting curve using a peptide nucleic acid according to a preferred embodiment of the present invention.

FIGS. 3 to 7 are nucleotide sequence views showing examples of the nucleotide sequences of portions and SNPs of VHSV NV gene and peptide nucleic acids derived therefrom, which are used in the present invention, wherein FIGS. 3 to 7 contain the following sequences: FIG. 3—FDC-VHS2013-1, AGATGACGACCCAGTCGGCA CACAGCACAACCAGCTTCTCTCCACTTGTCCTTCG TGAGA (SEQ ID NO: 9); FDC-VHS2012-6, AGATG ACGACCCAGTCGGCACACAGCACAACCAGCTTCT CT CCACTTGTCCTTCGCGAGA (SEQ ID NO: 10); FDC-VHS2014-5,AGATGACGACCCAGTCGGCACAC AGCACAACCAGCTTCTCTCCACTTGTCCTTCGCG AGA (SEQ ID NO: 10); FDC-VHS2013-9, AGATGACGA CCCAGTCGGCACACAACACAACCAGCTTCTCTCC ACTTGTCCTTCGCGAGA (SEQ ID NO: 11); FDC-VHS2016-2, AGATGACGACCCAGTCGGCA CACA ACACA ACCAGCTTCTCTCCACTTGTCCTTC GCG AGA (SEQ ID NO: 11); FDC-VHS2014-4, AGATGAC GACCCAGTCGGCACACAACACAACCAGCTTCTCTC-CACTTGTCCTTCGCGAGA (SEQ ID NO: 11); FDC-VHS2012-11, AGATGACGACCCAGTC GGCACACAGC ACAACCAGCTTCTCTCCACTTGTCCTTCGCGAGA (SEQ ID NO: 10); FDC-VHS2014-2, AGATGACGACC CAG TCGGCACACAGCACAACCAGCTTCT CTC-CACTTGTCCTTCGCGAGA (SEQ ID NO: 10); FDC-VHS2012-7, AGAT GACGACCCAGTCGGCACACAGC ACA ACCA GCTTCTCTCCACTTGTCCTTCGCGAGA (SEQ ID NO: 10); FDC-VHS2013-2, AGATGACG ACCCAGTCGGCACA CAGCACAACCAGCTTCTCTC-CACTTGTCCTTCGCGAGA (SEQ ID NO: 10); FDC-VHS2013-4, AGATGACGACCCAGTCGGCACACAG CAC AACCAGCTTCTCT CCACTTGTCCTTCGCGAGA (SEQ ID NO: 10); FDC-VHS2013-3, AGATGACGACT CAGTCGGCACACAGCACAACCAGCTTCTCTCCAC TTGTCCTTCGCGAGA (SEQ ID NO: 12); FDC-VHS2012-9, AGATGACGACTCA GTCGGCACACAG CAC AACCAGCTTCTCTCCACTTGTCCTTCGCGAGA (SEQ ID NO: 12); FDC-VHS2012-10, AGATGACGAC CCAGTCGGCACACAGCACA ACCAGCTTCTCTCCA CTTGTCCTTCGCGAGA (SEQ ID NO: 10); FDC-VHS 2016-1, AGATGACGACCCAGTCGGCACACAGCA CA A CCAGCTTCTCTCCACTTGTCCTTCGCGAGA (SEQ ID NO: 10); FIG. 4—FDC-VHS2013-1, CAGAAATC TCCGCTACAGACTTCTTCGAGACAACTCTCTCTA GAGTCTCAGAGGATCTAA (SEQ ID NO: 13); FDC-VHS2012-6, CAGAAATCTCCG CTACAGACTT CTTCG AAACAACTCTTCTAGAGTCTCAGAGGATCTAA (SEQ ID NO: 14); FDC-VHS2014-5, CAGAAATCTCCGCTA-CAGACTTCTTCGAGACA ACTCTTTCTAG AGTCTCA GAGGATCTAA (SEQ ID NO: 15); FDC-VHS2013-9, CAGAAATCTCCGCTACAGACTTCTTCGAGACAAC TCTTTCTAGAGTCTCAGAGGATCTAA (SEQ ID NO: 15); FDC-VHS2016-2CAGAAATCTCCGCTACAGA CT TCTTCGAGACAACTCTTTCTAGAGTCTCAGAGGA TCTAA (SEQ ID NO: 15); FDC-VHS2014-4, CAG AAATCTCCGCTACAGACTTCTTCGAGACAACTCTT TCTA GAGTCTCAGAGGATCTAA (SEQ ID NO: 15); FDC-VHS2012-11, CAGAA ATCTCCGATACAGACTTC TTCGAGAAAACTTTTCTAGAGTCTCAGAGGATCT AA (SEQ ID NO: 16); FDC-VHS2014-2, CAGAAA-TCTCCGCTACAGACTTCTTCGAGACAACTCTTTC-CAGAGTCTCAGAGGATCTAA (SEQ ID NO: 17); FDC-VHS2012-7, CAGAAATCTCCGCTACAGAATTCTTCG-AGACAACTCTTTCTAGAG TCTCAGAGGATCTAA (SEQ ID NO: 18); FDC-VHS2013-2CAGAA ATCTCCGC-TACAGATTCTTCGAGACAACTCTTTCTAGAGTCT-CA- GAGGATCTAA (SEQ ID NO: 19); FDC-VHS2013-4, CAGAAATTCCGCTA CAGAATTCTTCGAGACA-ACTC- TTTCTAGAGTCTCAGAGGATCTAA (SEQ ID NO: 20); FDC-VHS2013-3, CAGAAATCTCCGCTACA-GACTTCTTCGAGACA ACTCTTTCTAGAGTCTTAGA-GGATCTAA (SEQ ID NO: 21); FDC-VHS2012-9, CAGAAATCTCCGCTACAGACTTCTTCGAGACAA-CTCTCTATAGAGTCTCAGAGGATCTAA (SEQ ID NO: 22); FDC-VHS2012-10, CAGAAATCTCCGCTAC AGA-CTTCTTCGAGACAACTTTTCTAGAGTCTCAGAG-GATCTAA (SEQ ID NO: 23); FDC-VHS2016-1, CAGA-AATCTCCGCTACAGACTTCTTCGAGACAACTT TTCTAGAGTCTCAGAGGATCTAA (SEQ ID NO: 23); FIG. 5—FDC-VHS2013-1 ATCCTGGACTCTTCATCAT TTCACTTGAGGGAATGAAGACCTTGACGAATGGC TCCAAAT (SEQ ID NO: 24); FDC-VHS2012-6, ATC CTGGACTCTTCAT CATTTCACTTGAGGGAATGA A AACCTTGACGAATGGCTCCGAAT (SEQ ID NO: 25); FDC-VHS2014-5, ATCCTGGACTCTTCATCATTTCA CTTGAGGGAATGAAAA CCTTGACGAATGG CTC CGAAT (SEQ ID NO: 25); FDC-VHS2013-9, ATCCT GGACTCTTCATCATTTCACTTGAGGGAATGAAAA CCTTGACGAATGGCTCCGAAT (SEQ ID NO: 25); FDC-VHS2016-2, ATCCTGGACTCTTCATCATTTCACTTGA GGGAATGAAAACCTTGACGAATGGCTCCGAAT (SEQ ID NO: 25); FDC-VHS2014-4, ATCCTGGAC TCTTCA TCATTTCACTTGAGGGAATGAAAACC TTG ACGAATGGCTCCGAAT (SEQ ID NO: 25); FDC-VHS2012-11, ATCCTGGACTCTTCATCATTTCACTT-GAGGG AATGAAAACCTTGACGAATGGCTCCGAAT (SEQ ID NO: 25); FDC-VHS2014-2, ATCCTGGACTCTT-CATCATTTCACTTGAGGGAATGAAAACCTTGACGA ATGGCTCCGAGT (SEQ ID NO: 26); FDC-VHS2012-7, ATCCTGGACTCTT CATCATTTCACTTGAGGGAAT-GAAAACCTTAACGAATGGCTCCGAAT (SEQ ID NO: 27); FDC-VHS2013-2, ATCCTGGACTCTTCATCATTT-CACTTGAGGGAA TGAAAACCTTGACGAATGGCTC CGAAT (SEQ ID NO: 25); FDC-VHS2013-4, ATCC TGGACTCTTCATCATTTCACTTGAGGGAATGAAA ACCTTGACGAATGGCTCCGAAT (SEQ ID NO: 25); FDC-VHS2013-3, ATCCTGGACTCTTCAT CATTTCAC TTGAGGGAATGAAAACCTTGACGAATGACTCC GAAT (SEQ ID NO: 28); FDC-VHS2012-9, ATC CTGGACTCTTCATCATTTCACTTGAGGGAATGAA AA CCTTGACGAATGGCTCCGAAT (SEQ ID NO: 25); FDC-VHS2012-10, ATCCTGGACTCTTCATCATTTCA CTTGAGGGAATGAAAACCTTGACGAATGGCT CC GAAT (SEQ ID NO: 25); FDC-VHS2016-1, ATCCT GGACTCTTCATCAT TTCACTTGAGGGAATGAAAAC CTTGACGAATGGCTCCGAAT (SEQ ID NO: 25); FIG. 6—FDC-VHS2013-1, ACATGAGGATAAGTCTCCTAG AG GGAGCTCAT TACACTAAGGAATGTCCCCTCCA GTCCT SEQ ID NO: 29); FDC-VHS2012-6, ACATGAG-GATAAGTCTTCTAGAGGGAACTCATTACATTAAGG AATGTCCCCTCCAGTCCT (SEQ ID NO: 30); FDC-VHS2014-5, ACATGAGGATAAGTCT TCTAGAGGGA ACTCATTACATTAAGGAATATCCCCTCCAGTCCT (SEQ ID NO: 31); FDC-VHS2013-9, ACATGAGGA-TAAGTCTTCTAGAGGGAACTCATTACAT TAAGG AA TGTCCCCTCCAGTCCT (SEQ ID NO: 32); FDC-VHS2016-2, ACATGAGGATAAGTCTTCTAGAGGGA ACTCATTACATTAAGGAATGTCCCCTCCAGTCCT (SEQ ID NO: 30); FDC-VHS2014-4, ACATGAGGA-TAAGTCTTC TAGAGGGAACCCATTACATTAAGGA ATGTCCCCTCCAGTCCT (SEQ ID NO: 33); FDC-VHS2012-11, ACATGAGGATAAGTCTTCTAGAGGGAA CTCATTACACTA AGGAATGTCCCCTCCAGTCCT (SEQ ID NO: 34); FDC-VHS2014-2, ACATGAGGA-TAAGTCTTCTAGAGGGAACTCATTACACTAAGGAA TGTCCCCTCCAGTCCT (SEQ ID NO: 34); FDC-VHS2012-7, ACATGAGGATAA GTCTTCTAGAGG-GAACTCATTACACTAAGGAATGTCCCCTCCAGTCCT (SEQ ID NO: 34); FDC-VHS2013-2, ACATGAGGA-TAAGTCTTCTAGAG GGAACTCATTACATTAAG GAA TGTCCCCTCCAGTCCT (SEQ ID NO: 30); FDC-VHS2013-4, ACATGAGGATAAGTCTTCTAGAGG-GAACTCA TACATTAAGGAAT GTCCCCTCCAGTCCT (SEQ ID NO: 35); FDC-VHS2013-3, ACATGAGGATAA GTCTTCTAGAGGGAACTCATTACATTAAGGAATG TCCCCTCCAGTCCT (SEQ ID NO: 30); FDC-VHS2012-9, ACATGAGGATAAGTCTTCTAGAGGGAACT CAT-TACATTAAGGAATGTCCCCTCCAGTCCT (SEQ ID NO: 30); FDC-VHS2012-10, ACATGAGGATAAGTC TTCTAGAGGGAACTCATTACATTAAGGAATGTCCC CTCCAGTCCT (SEQ ID NO: 30); FDC-VHS2016-1, ACATGAGGATAAGT CTTCTAGAGGGAACTCATTA-CATTAAGGAATGTCCCCTCCAGTCCT (SEQ ID NO: 30); and FIG. 7—FDC-VHS2013-1, GAATGGCTC-CAAATCTCCCCCATGAAC TCCTTCCCCTTCTCCCA-GATAGAAAAAAATGGC (SEQ ID NO: 36); FDC-VHS2012-6, GAATGGCTCCGAATC TCCCCCATGAA CTCCTCCCCCTTCTCCCAG ATAGAAAAAAATGGC (SEQ ID NO: 37); FDC-VHS2014-5, GAATG GCTCCGA ATCTCCCCCATGAACTCCTCCCCCTTCTCCCAGA-TAGAAAAAAATGGC (SEQ ID NO: 37); FDC-VHS2013-9, GAATGGCTCCGAATCTCCC CCATGAACTCCTC C CCCTTCTCCCAGATAGAAAAAAATGGC (SEQ ID NO: 37); FDC-VHS2016-2, GAATGGCTCCGAATCTCCCC-CATGAACTCCTCCCCCTTCTCC CAGATAGAAAAA AATGGC (SEQ ID NO: 37); FDC-VHS2014-4, GAATGGCTCCGAATCTCCCCCATGAACTCCTC CC CCTTCTCCCAGATAGAAAAAAATGGC (SEQ ID NO: 37); FDC-VHS2012-11, GAATGGCTCCGAATCTC CCC-CATGAACTCCTCCCCCTTCTCCCAGATAGAAAA AAATGGC (SEQ ID NO: 37); FDC-VHS2014-2, GAA TGGCTCCGAGTCTCCCCCATGAACTCCTCCCCCTT CTCCCAGATAGAAAAAAATGGC (SEQ ID NO: 38); FDC-VHS2012-7, GAATGGCTCCGAATCTCCCCCATG AACTCCTCCTCCTTCTCCCAGATAGAAAAAA ATG GC (SEQ ID NO: 39); FDC-VHS2013-2, GAATGGCT CCGAATCTCC CCCATGAACTCCTCCCCCTTCT CCC AGATAGAAAAAAATGGC (SEQ ID NO: 37); FDC-VHS2013-4, GAATGGCTCCGAATCTCCCCCATGAAC TCCTCCCCCTTCTCC CAGATAGAAAAAAATGGC (SEQ ID NO: 37); FDC-VHS2013-3, GAATGACTCCGAA TCTCCCCCATGAACTCCTCCCCCTTCTCCCAGA-TAGAAAAAAATGGC (SEQ ID NO: 40); FDC-VHS2012-9, GAATGGCTCCGA ATCTCCCCCATGAACTCCTCC CCCCTCTCCCAGATAGAAAAAAATGGC (SEQ ID NO: 41); FDC-VHS2012-10, GAATGGCTCCGAATCTCCCC-CAT GAACTCCTCCCCCTTCTCCCAGATAGAAAAA AATGGC (SEQ ID NO: 37); FDC-VHS2016-1, GAATGGC TCCGAATCTCCCCCATGAACTCCTCCCCCTTCTC CCAG ATAGAAAAAAATGGC (SEQ ID NO: 37).

FIG. 8 is a gene position view illustrating examples of major nucleotide variations included in peptide nucleotide acids on VHSV NV gene amplification products according to the present invention.

FIG. 9 is a graph illustrating a process of amplifying a VHSV cDNA sample, hybridizing a PNA probe to the amplification product, and increasing the temperature of the hybridization product according to the present invention.

FIG. 15 is a table (Analysis of melting temperatures of 15 VHSV samples), summarizing the melting temperature on melting curve of each PNA probe for each sample.

FIG. 16 is a table (Relationship between the melting temperatures of PNA probes included in set 1 and the nucleotide sequences), showing the melting temperature comparatively analyzed with the nucleotide sequences for set 1.

FIG. 17 is a table (Relationship between the melting temperatures of PNA probes included in set 2 and the nucleotide sequences), showing the melting temperature comparatively analyzed with the nucleotide sequences for set 2.

FIG. 18 is a table (Conversion of melting temperature values of PNA probes into barcodes by use of judgment table), showing Tm values converted into barcodes.

FIG. 19 is a table (Detection of mutations by data indicated by barcodes), showing nucleotide sequence mutations can be detected using barcodes that imply the results.

BEST MODE FOR CARRYING OUT THE INVENTION

Figure 1:
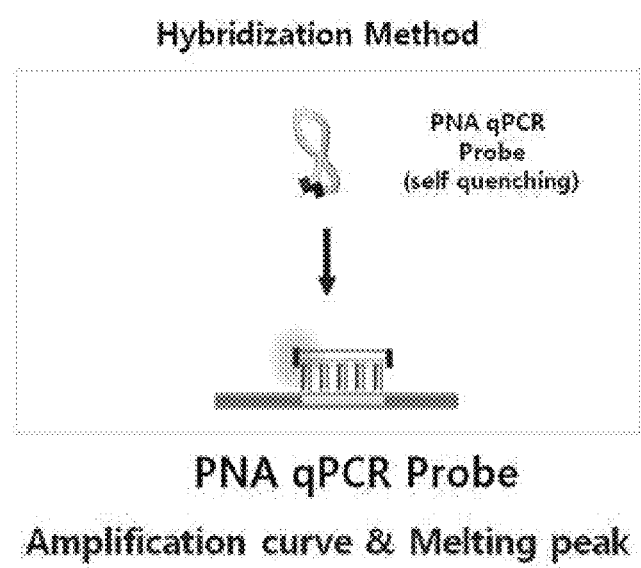
FIG. 1 shows the structural characteristic of a PNA probe.
Figures 2, 3:
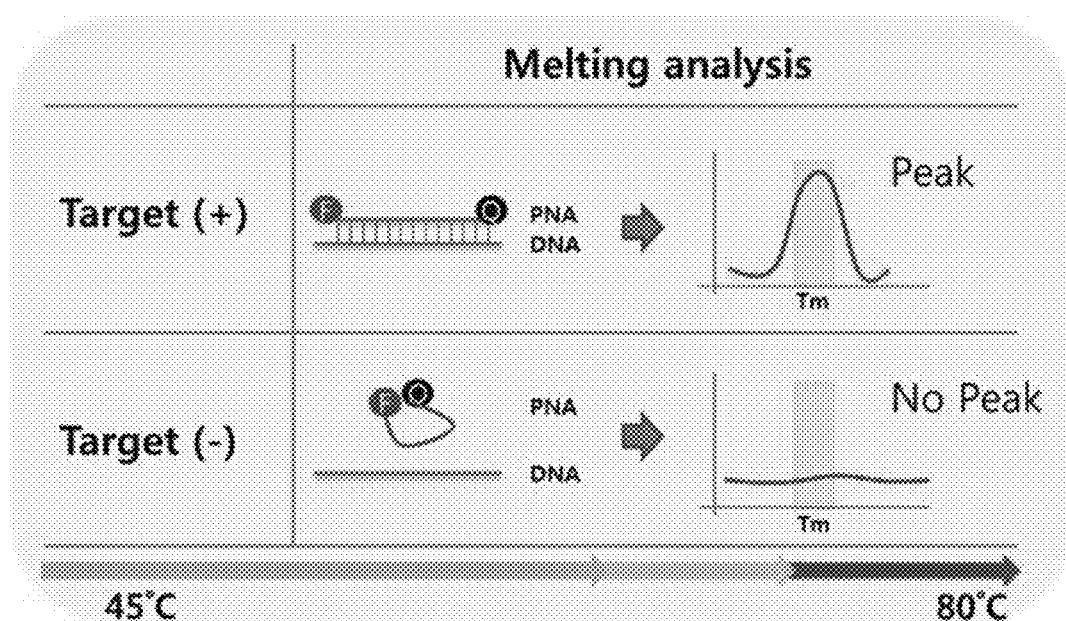

Unless defined otherwise, all technical and scientific terms used herein have the same meaning as commonly understood by one of ordinary skill in the art to which the invention pertains. Generally, the nomenclature used herein and the experiment methods, which will be described below, are those well known and commonly employed in the art.

In one embodiment of the present invention, the present inventors have attempted to detect a nucleotide sequence mutation in the non-viron (NV) gene of VHSV, which is a virus that causes infectious aquatic organism diseases as set forth in the Aquatic Animal Health Code of the World Organization for Animal Health (OIE), without a sequencing step. As a result, using a nucleotide sequence specific for the VHSV non-viron (NV) gene and a peptide nucleic acid probe (PNA probe), a mutation in the VHSV non-viron (NV) gene could be identified or detected.

Therefore, in one aspect, the present invention is directed to a method of determining a mutation in viral hemorrhagic septicemia virus (VHSV) non-viron (NV) gene by use of a PNA probe having attached thereto a reporter and a quencher, the method comprising the steps of:

(a) hybridizing the PNA probe to a sample by mixing (i) a sample containing either viral hemorrhagic septicemia virus (VHSV) or a target nucleic acid comprising a mutation site of the viral hemorrhagic septicemia virus (VHSV) non-viron (NV) gene, and (ii) a PNA probe that binds complementarily to the nucleotide sequence of the target nucleic acid comprising the mutation site of the viral hemorrhagic septicemia virus (VHSV) NV gene;

(b) obtaining a melting temperature of the hybridization product while changing the temperature of the hybridization product;

(c) assigning a code after sectionalizing the melting temperature of the hybrization product; and (d) reacting a sample expected to have mutation under the same conditions as steps (a) to (b) to thereby obtain the melting temperature of the sample, and encoding the obtained melting temperature referring to the assigned code of step (c), thereby determining the type of the mutation in viral hemorrhagic septicemia virus (VHSV) non-viron (NV) gene.

As used herein, the term "mutation type" means the presence or absence of mutation and the position of mutation.

In the present invention, the PNA probe may have a sequence represented by any one of SEQ ID NOs: 1 to 6, and the PNA probe may be either a PNA probe set represented by SEQ ID NOs: 1 to 3 or a PNA probe set represented by SEQ ID NOs: 4 to 6.

In the present invention, the PNA probe may have a reporter and a fluorescence quencher attached to both ends. The fluorescence quencher can quench the fluorescence of the reporter. The reporter may be one or more selected from the group consisting of FAM (6-carboxyfluorescein), Texas red, HEX (2',4',5',7'-tetrachloro-6-carboxy-4,7-dichloro-fluorescein), JOE, Cy3, and Cy5. The quencher may be one or more selected from the group consisting of TAMRA (6-carboxytetramethyl-rhodamine), BHQ1, BHQ2 and Dabcyl, but is not limited thereto.

Peptide nucleic acid (PNA) is a DNA analogue having nucleic acid nucleotides connected by peptide bonds, but not phosphate bonds, and was first synthesized by Nielsen et al. in 1991. PNA is artificially synthesized by a chemical method, but not found in natural systems.

PNA is one of substances that recognize genes, like LNA (locked nucleic acid) or MNA (morpholino nucleic acid). It is artificially synthesized and has a backbone consisting of polyamide. PNA has advantages in that it has very high affinity and selectivity, and has a high stability for nuclease so that it is not cleaved by an existing restriction enzyme. In addition, PNA advantageously is thermally and chemically highly stable so that it is easily stored and is not readily degraded.

PNA forms a duplex by its hybridization to a natural nucleic acid having a nucleotide sequence complementary thereto. When their lengths are equal, a PNA/DNA duplex is more stable than a DNA/DNA duplex, and a PNA/RNA duplex is more stable than a DNA/RNA duplex. Furthermore, since PNA has a single base mismatch that makes the duplex very unstable, the ability of PNA to detect SNP (single nucleotide polymorphism) is better than that of natural nucleic acid.

Although the length of the PNA nucleotide sequence according to the present invention is not particularly limited, it may be constructed to have a length of 12 to 18-mer so as to contain a specific nucleotide sequence (e.g., nucleotide variation or single nucleotide polymorphism (SNP)) depending on the kind of virus. In the present invention, a PNA probe may be designed to have a desired $T_m$ value by adjusting the length of the PNA probe, and even in the case of PNA probes having the same length, the Tm value may be adjusted by changing the nucleotide sequence. Furthermore, since a PNA probe has a binding affinity higher than a DNA probe, it has a higher $T_m$ value. Thus, the PNA probe can be designed to have a length shorter than a DNA probe, so that it can detect even adjacent nucleotide variation or SNP. In a conventional high-resolution melt (HRM) method, a difference in Tm value is very small (about 0.5° C.). For this reason, when two or more nucleotide variations appear, they cannot match with nucleotide sequence variations. However, the PNA probe according to the present invention shows a distinct difference in Tm values between nucleotide positions, and thus can be analyzed.

In one embodiment of the present invention, a code assigned to the melting temperature between the target nucleic acid and the PNA probe may be different from a code assigned to the melting temperature between the mutation in the target nucleic acid and the PNA probe.

The present invention also provide information obtained by encoding the melting temperature between the target nucleic acid and the probe and the melting temperature between the mutation in the target nucleic acid and the probe in order to determine the mutation in the target nucleic acid.

In one embodiment of the present invention, the melting temperature between the target nucleic acid and the PNA probe and the melting temperature between the mutation in the target nucleic acid and the PNA probe may be expressed or sectionalized as different temperature zones and may be assigned with different codes.

In one example of the present invention, the melting curve of the VHSV NV gene was analyzed using a nucleotide sequence mutation tracking code method. As a result, it was shown that the melting temperatures were the same or different depending on the absence or presence of a mutation in the nucleotide sequence of a sample that binds to a single PNA probe, but when analyses were simultaneously performed using two or more PNA probes, a combination of the melting temperatures did vary depending on the type of VHSV sample. When this characteristic is used, reference codes based on probes can be made, and as a result, codes can be assigned as shown in FIG. 18. As such, when a PNA probe does not completely hybridize to the nucleotide sequence of a sample, the melting temperature is downshifted, and thus a change in the nucleotide sequence can be tracked. Furthermore, a series of codes are assigned to melting temperatures resulting from changes in the nucleotide sequence, there is an advantage in that when large amounts of samples are infected with VHSV, tracking of the samples is possible. In addition, when the melting temperatures of fresh samples are classified according to previously assigned codes, the type of samples can be easily determined. In this case, a rapid and effect method for preventing various infectious diseases from spreading rapidly due to the occurrence of mutations in nucleotide sequences can be provided.

As shown in FIG. 19, when the code method according to the present invention is used, there is an advantage in that various infectious diseases which require tracking can be detected without having to use other programs, by constructing minimal PNA probes that bind complementarily to nucleotide sequences in which a mutation frequently occurs, and encoding the melting temperature of the PNA probes.

In the case of the tracking method of the present invention, a single PNA probe shows various melting temperatures depending on changes in the nucleotide sequences. Thus, when these melting temperatures are suitably combined and expressed as numerical values, information about each sample can be determined. Furthermore, when the range of melting temperatures is sectionalized and expressed as temperature zones, information about large amounts of samples can be encoded using a small number of PNA probes. Melting temperatures can be sectionalized as temperature zones in the range from 40 to 95° C., in which melting curves can be measured, or in the range from 5 to 95° C., in which particular devices are used. However, there may be a case in which the same melting temperature appears, although the positions of mutations in nucleotide sequences differ. In this case, additional PNA probes may be constructed to make discrimination possible. This code method can prevent time and cost waste by selectively using a specific drug or vaccine corresponding to a sample classified as the same code in reference codes, without having to use many vaccines or drugs in providing methods for preventing the spreading of infectious diseases against which rapid measures are required, in case of emergency.

In another aspect, the present invention is directed to a kit for confirming the position of a nucleotide sequence mutation in viral hemorrhagic septicemia virus (VHSV) non-virion (NV) gene, the kit comprising a plurality of PNA probes, each of which has a reporter and a quencher attached thereto, binds complementarily to the viral hemorrhagic septicemia virus (VHSV) non-virion (NV) gene, and has a nucleotide sequence selected from SEQ ID NOs: 1 to 6.

The kit of the present invention may optionally include reagents required for performing a target nucleic acid amplification reaction (e.g., PCR reaction), such as buffer, DNA polymerase cofactor, and deoxyribonucleotide-5-triphosphate. In addition, the kit of the present invention may also comprise various polynucleotide molecules, a reverse transcriptase, various buffers and reagents, and an antibody that inhibits the activities of a DNA polymerase. In addition, in the kit, the optimal amount of the reagent used in a specific reaction can be easily determined by those skilled in the art who have acquired the disclosure set forth herein. Typically, the kit of the invention may be manufactured as a separate package or compartment comprising the above mentioned ingredients.

When the kit is used, a single nucleotide variation and a mutation caused by nucleotide deletion or insertion in a target nucleic acid can be effectively detected by analysis of a melting curve obtained using the PNA, thereby detecting viral mutation.

In another embodiment of the present invention, for viral hemorrhagic septicemia virus (VHSV), gene nucleotide sequences corresponding to PCR products were comparatively analyzed, and based on the results of the analysis, a PNA probe represented by each of nucleotide sequences of SEQ ID NOs: 1 to 6 was hybridized to a PCR amplification product amplified using a detection primer pair represented by SEQ ID NOs: 7 and 8, thereby obtaining melting curves. From the melting curves, the melting temperature (Tm) was determined, so that the mutation in the NV gene of viral hemorrhagic septicemia virus (VHSV) could be identified and detected.

In the present invention, a step of amplifying a sequence fragment comprising the NV gene nucleotide sequence of the viral hemorrhagic septicemia virus contained in the mixture may be performed using a primer pair having nucleotide sequences represented by SEQ ID NOs: 7 and 8.

As used herein, the term "sample" is meant to include various samples. Preferably, a biosample is analyzed using the method of the present invention. More preferably, the sample may be either a sample that is mixed with the bacterial species of *Edwardsiella tarda* and/or *Streptococcus*, or a sample from an individual (for example, fish or the like) infected with the bacteria. Biosamples originated from plants, animals, humans, fungi, bacteria and virus can be analyzed. When a mammal- or human-originated sample is analyzed, it may be derived from specific tissues or organs. Representative examples of tissues include connective tissue, muscle, or nerve tissue. Representative examples of organs include eyes, brain, lung, liver, spleen, bone marrow, thymus, heart, lymph, blood, bone, cartilage, pancreas, kidney, gallbladder, stomach, small intestine, testis, ovary, uterus, rectum, nervous system, and gland and internal blood vessels. A biosample to be analyzed includes any cell, tissue or fluid that is derived from a biological origin, or any other medium that can be well analyzed by the present invention. The biosample also includes a sample obtained from foods produced for consumption of humans and/or animals. In addition, the to-be-analyzed biosample includes a body fluid sample, which includes, but not limited to, blood, serum, plasma, lymph, breast milk, urine, feces, ocular fluid, saliva, semen, brain extracts (e.g., grinded brain), spinal fluid, and extracts from appendix, spleen, ortonsil tissue, but not limited thereto.

As used herein, the term "target nucleic acid" means a nucleic acid sequence (containing SNP) to be detected. The target nucleic acid comprises a specific region of the nucleic acid sequence of a "target gene" encoding a protein having physiological and biochemical functions, and is annealed or hybridized to the primer or the probe under annealing, hybridization, or amplification conditions.

As used herein, the term "hybridization" means that complementary single-stranded nucleic acids form a double-stranded nucleic acid. Hybridization can occur when the complementarity between two nucleic acid strands is perfect (perfect match) or when some mismatched residues exist. The degree of complementarity necessary for hybridization may vary depending on hybridization conditions, particularly may be controlled by temperature.

In the present invention, the melting curve analysis may be performed by a fluorescence melting curve analysis (FMCA) method.

The PNA probe comprising the reporter and the quencher according to the present invention generates a fluorescent signal after its hybridization to the target nucleic acid. As the temperature increases, the PNA probe is rapidly melted with the target nucleic acid at its suitable melting temperature, and thus the fluorescent signal is quenched. Through analysis of a high-resolution melting curve obtained from the fluorescent signal according to temperature changes, the presence or absence of a nucleotide modification (including nucleotide variation or SNP) may be detected. If the PNA probe perfectly matches with the nucleotide sequence of the target nucleic acid, it then shows an expected melting temperature ($T_m$) value, but if the PNA probe mismatches with a target nucleic acid in which a nucleotide variation is present, it shows a melting temperature ($T_m$) value lower than an expected value.

As used herein, the term "nucleotide variation" refers to a change in a nucleotide sequence of a target nucleic acid (e.g., a substitution, deletion or insertion of one or more nucleotides, as well as a single nucleotide polymorphism (SNP)) relative to a reference sequence. The PNA probe of the present invention can analyze a change in a nucleotide sequence of a target nucleic acid such as SNP of the target nucleic acid or a substitution, deletion or insertion of nucleotides of the target nucleic acid through the melting curve analysis.

The $T_m$ value also changes depending on the difference between the nucleotide sequence of the PNA probe and the nucleotide sequence of a DNA complementary thereto, and thus the development of applications based on this change is easily achieved. The PNA probe is analyzed using a hybridization method different from a hydrolysis method used for a TaqMan probe, and probes having functions similar to that of the PNA probe include molecular beacon probes and scorpion probes.

A specific nucleotide sequence (e.g., nucleotide variation or SNP) analysis using the PNA probe can be sufficiently achieved using a forward/reverse primer set (according to Office of International Epizootics (OIE) standards for the conventional primer pair) for PCR and a probe comprising nucleotide(s) that recognize(s) the specific nucleotide sequence, and a primer of producing a single-strand genetic marker sequence fragment using a genetic marker nucleotide sequence amplified by the primer set as a template. The PCR may be performed using a conventional method, and after completion of the PCR, a melting process is required. Whenever the melting temperature increases by 0.5° C., the intensity of fluorescence is measured to obtain the Tm value. In particular, general real-time PCR systems are widely known and have an advantage in that purchase of an additional program such as a HRM (high-resolution melting) program or a minute temperature change is not required.

Melting curve analysis according to the present invention is a method of analyzing a double-chain nucleic acid formed of the target nucleic acid DNA or RNA and the probe. This method is called "melting curve analysis", because it is performed by, for example, $T_m$ analysis or the analysis of the melting curve of the double-strand nucleic acid. Using a probe complementary to a specific nucleotide sequence (including nucleotide variation or SNP) of a target to be detected, a hybrid (double-chain DNA) of a target single-chain DNA and the probe is formed. Subsequently, the formed hybrid is heated, and the dissociation (melting) of the hybrid, which results from an increase in the temperature, is detected based on a change in a signal such as absorbance. Based on the results of the detection, the Tm value is determined, so that the presence or absence of the specific nucleotide sequence can be determined. The $T_m$ value increases as the homology of the formed hybrid increases, and the $T_m$ value decreases as the homology decreases. For this reason, the $T_m$ value of a hybrid formed of a specific nucleotide sequence of a target to be detected and a probe complementary thereto is previously determined (a reference value for evaluation), and the $T_m$ value of a hybrid formed of the target single-chain DNA of a sample to be detected and the probe is measured (a measured value). If the measured value is approximately equal to the reference value, it can be determined that the probe matches, that is, a specific nucleotide sequence is present in the target DNA. If the measured value is lower than the reference value, the probe mismatches, that is, mutation is present in the target DNA or there is no target DNA in the sample.

The fluorescent melting curve analysis of the present invention is a method that analyzes a melting curve using a fluorescent material, and more specifically, may analyze the melting curve by using a probe containing a fluorescent material. The fluorescent material may be either a reporter or a quencher, and may preferably be an intercalating fluorescent material.

In the present invention, the amplification may be performed by a real-time Polymerase Chain Reaction (PCR).

In the real-time polymerase chain reaction (PCR) method according to the present invention, a fluorescent substance is intercalated into a double-stranded DNA duplex during PCR, and the temperature is increased together with amplification to melt the DNA double strands to thereby reduce the amount of fluorescent substance present between the DNA double strands. The resulting melting curve pattern, particularly the temperature ($T_m$) at which the DNA is melted (denatured), may be analyzed, thereby detecting and/or determination the type of virus based on the presence or absence of the specific nucleotide sequence (including nucleotide variation or SNP).

As a technical method for optimizing the results of the present invention, a liquid type U-TOP method (Seasun Biomaterials, Korea) may be used. This method is a liquid type array method which uses a PNA probe having attached thereto a reporter and a quencher, which can effectively detect a single nucleotide substitution, deletion or insertion of a target nucleic acid. This method does not require a washing process following a hybridization process, and also does not require a process of immobilizing the PNA probe onto a plate.

EXAMPLES

Hereinafter, the present invention will be described in further detail with reference to examples. It will be obvious to a person having ordinary skill in the art that these examples are illustrative purposes only and are not to be construed to limit the scope of the present invention.

Example 1: Preparation of Peptide Nucleic Acids for Detecting Mutation in VHSV NV Gene cDNA templates obtained from viral samples infected with VHS, stored in the National Institute of Fisheries Science, were sequenced, and whether the sequences would be consistent with nucleotide sequences described in the guideline of the World Organization for Animal Health (OIE). Among the stored samples, samples identified as VHSV were used.

Mutations in the NV gene were detected by nucleotide sequencing, and a total of 6 major mutation regions were designed so that they would be detected using PNA probes. Primers and PNA probes for detecting mutations in cDNA were prepared (Table 1).

FIGS. 3 to 7 shows gene position views illustrating six VHSV NV gene mutation sites and SNPs and examples of PNA probe nucleotide sequences derived therefrom, which are used in the present invention. Herein, the PNA probe nucleotide sequences are indicated by yellow shadows, and the mutation sites and SNPs are indicated by red bolds.

Figures 7, 8, 9:
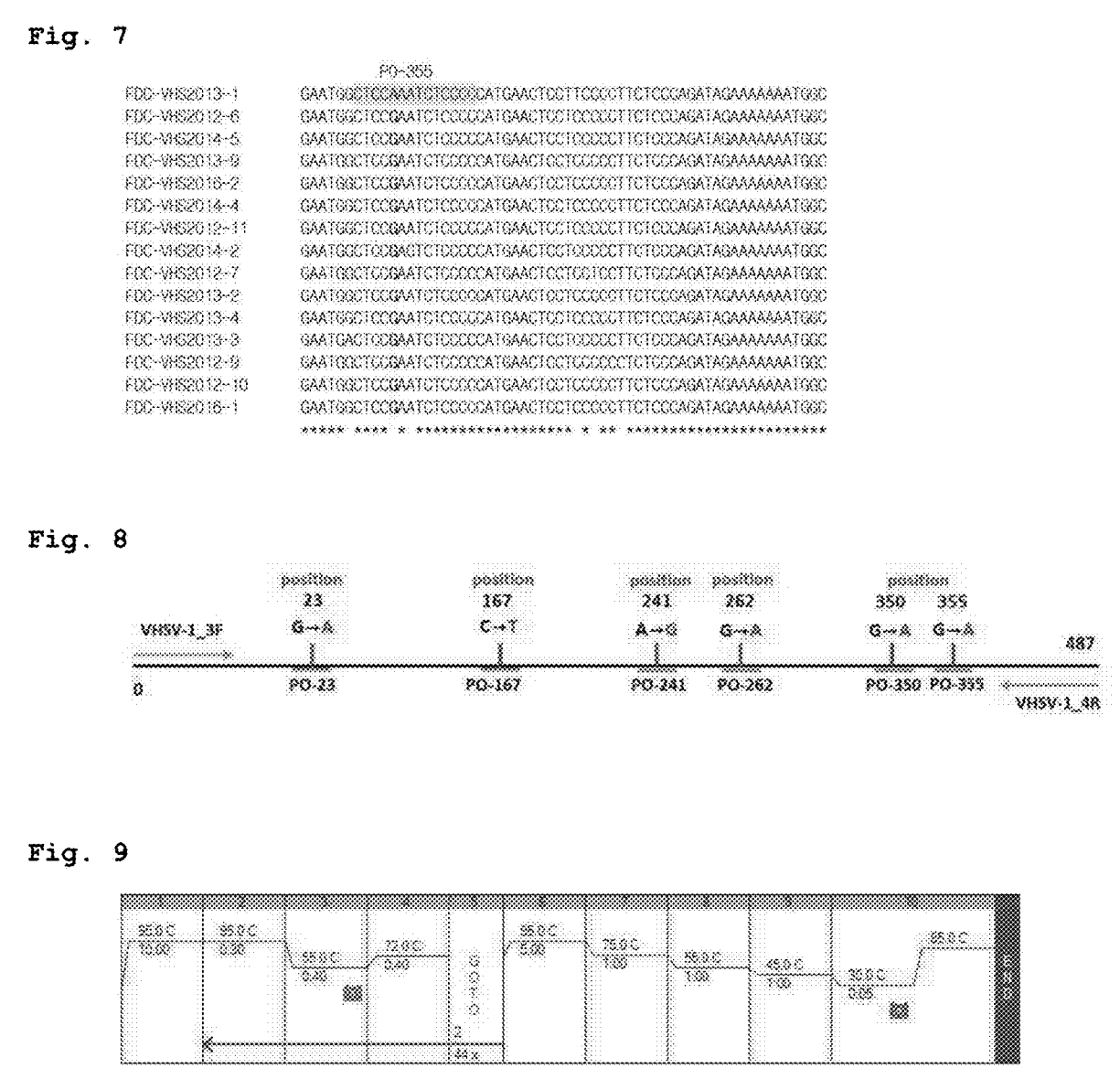

FIG. 8 is a gene position view illustrating examples of nucleotide variation sites on the VHSV NV gene, which are included in PNA probes. Each nucleotide number was based on the size of the PCR product of NV gene, which can be expressed as NV protein.

Example 2: Derivation of Amplification Curves and Melting Curves Using Peptide Nucleic Acids for Detecting VHSV NV Gene Mutations cDNA was obtained from VHSV (that is RNA virus) and used in experiments. Extraction of RNA was performed using TRIzol RNA isolation reagents (Thermo, USA), cDNA was obtained using M-MLV reverse transcriptase (Enzynomics, Korea) and used in experiments.

In order to obtain amplification curves and melting curves for VHSV samples by use of PNA probes, amplification reactions were performed in a CFX96™ real-time system (Bio-Rad Laboratories Inc., USA). Two sets were subjected to PCR reactions in two tubes, respectively, and used in experiments. The composition of PCR reactants is as follows: 10 µl of 2×qPCR PreMix buffer (Seasun Biomaterials, Korea), 0.5 µl (1 pmol) of VHSV-1_3F (forward primer), 0.5 µl (10 pmol) of VHSV-1_4R (reverse primer), 1 µl of VHSV cDNA (sample), 0.5 µl (2.5 µmol) of peptide nucleic acid, 20×SSB buffer (Seasun Biomaterials, Korea) and distilled water. The total volume of the composition was 20 µl.

FIG. 9 is a graph illustrating a process of amplifying a VHSV cDNA sample according to the present invention, hybridizing a PNA probe to the amplification product, and increasing the temperature of the hybridization product. The real-time PCR process was performed under the following conditions: denaturation at 95° C. for 10 min, and then repetition of 45 cycles, each consisting of 95° C. for 30 sec, 55° C. for 40 sec (fluorescence photographing), and 72° C. for 40 sec, thereby obtaining an amplification curve. Thereafter, to conduct hybridization to the PNA probe and obtain a melting curve, melting curve analysis was performed by performing reaction at 95° C. for 5 min, 75° C. for 1 min,

TABLE 1

Nucleotide sequences of primers and PNA probes for detecting mutations in VHSV VN gene

| Target gene | Classification | Name | Sequence (5→3) | SEQ ID NO: |
|---|---|---|---|---|
| NV gene | Primer | VHSV-1_3F | AAAATGGCACCCCTGTGAG | SEQ ID NO: 7 |
| | | VHSV-1_4R | GTATTACCCCCTGTAGGG | SEQ ID NO: 8 |
| | PNA probe | PO-23 | dabcyl-ACACAGCACAACC-O-K(TxR) | SEQ ID NO: 1 |
| | | PO-167 | dabcyl-AGTCTCAGAGGATC-O-K(HEX) | SEQ ID NO: 2 |
| | | PO-241 | dabcyl-AGAGGGAACTCAT-O-K(FAM) | SEQ ID NO: 3 |
| | | PO-262 | (HEX)-CTAAGGAATGTCCC-O-K(dabcyl) | SEQ ID NO: 4 |
| | | PO-350 | dabcyl-ACGAATGGCTCC-O-K(FAM) | SEQ ID NO: 5 |
| | | PO-355 | dabcyl-CTCCAAATCTCCCC-O-K(TxR) | SEQ ID NO: |

Because fluorescence that can be simultaneously detected by a real-time PCR system is limited, two tubes were used for detection, and the tubes contained peptide nucleotide acids labeled with different fluorescent dyes. Set 1 contained SEQ ID NOS: 1 to 3, and set 2 contained SEQ ID NOS: 4 to 6.

All the PNA probes used in the present invention were synthesized using a HPLC purification method by Panagene (Korea). The purities of the synthesized probes were analyzed by mass spectrometry (the unnecessary secondary structure of the probes was avoided for effective binding to a target nucleic acid).

55° C. for 1 min, and 45° C. for 1 min, and then performing fluorescence measurement while rising temperature from 30° C. to 85° C. at a rate of 1° C. with a stop state maintained for 5 sec between each step.

Figure 10:
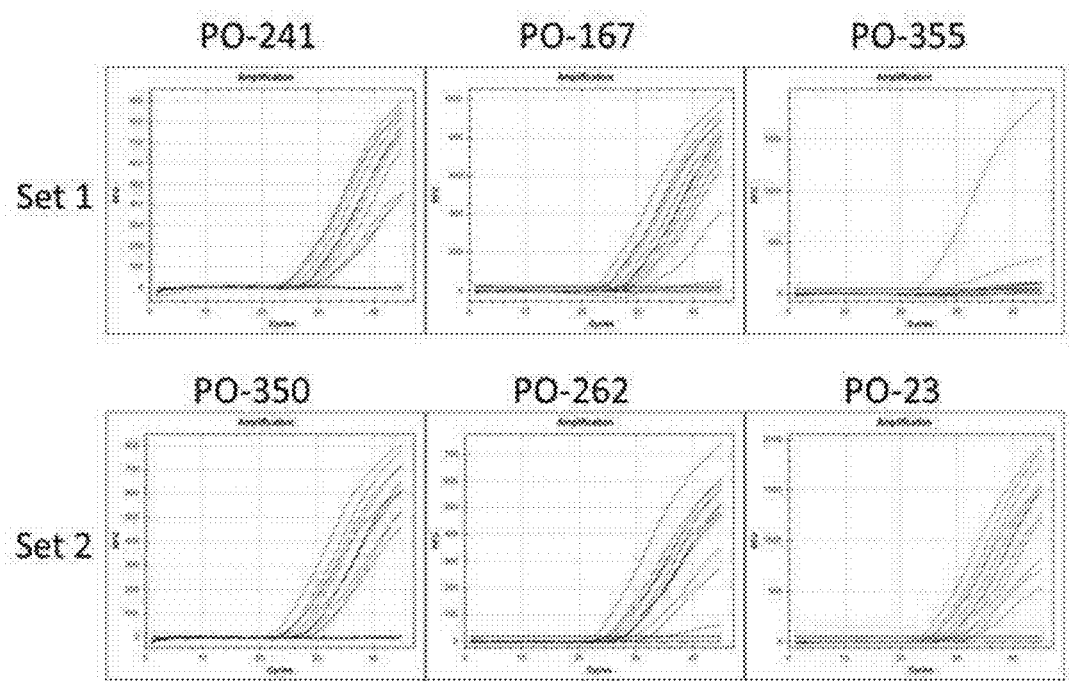
FIG. 10 shows examples of amplification curves obtained by applying peptide nucleic acids to VHSV cDNA samples in the present invention.

Example 3: Analysis of Amplification Curves and Melting Curves Using Peptide Nucleic Acids for Detection of VHSV NV Gene Mutations Amplification curves obtained in Example 2 are shown in FIG. 10. As can be seen therein, whether or not the gene would be amplified could be confirmed, and it was confirmed that the sample was amplified according to each fluorescence.

Figures 11, 12:
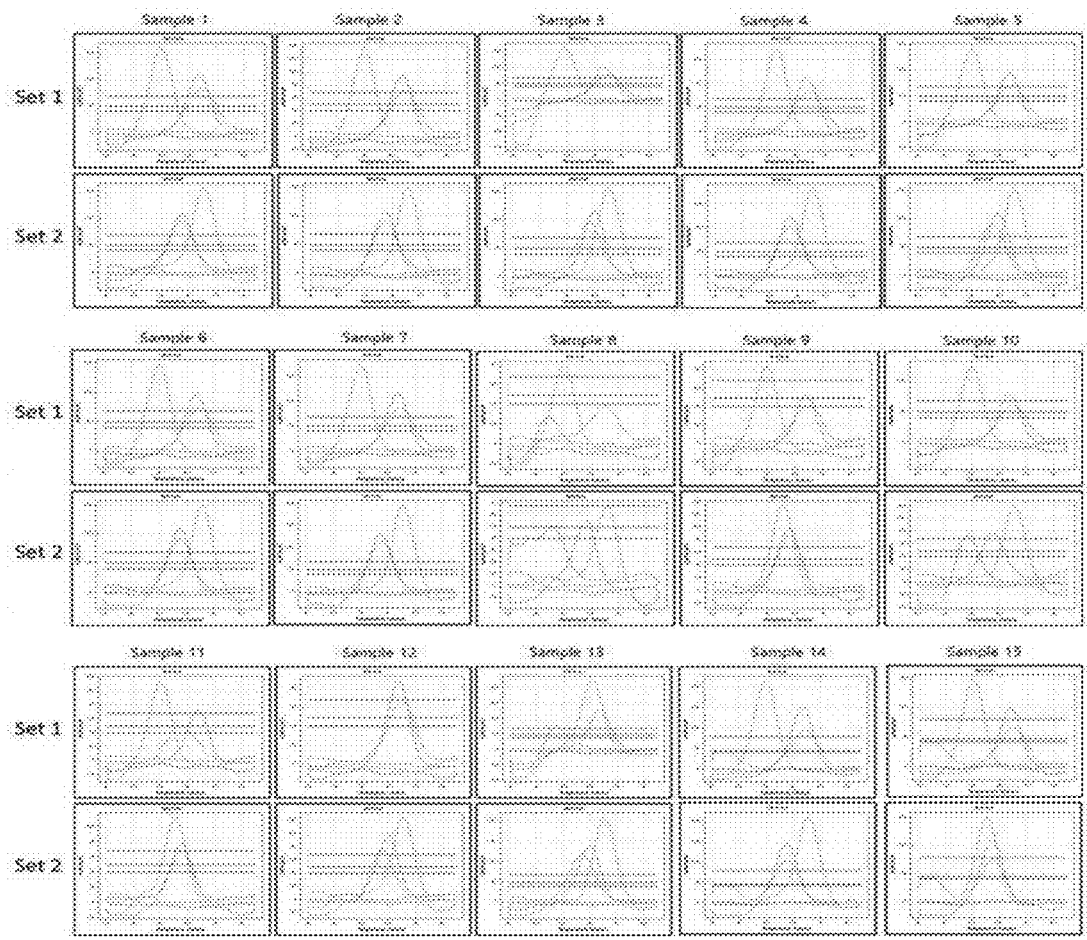
FIG. 11 shows examples of temperature-dependent melting curves obtained by applying peptide nucleic acids to VHSV cDNA samples in the present invention.
FIG. 12 shows a series of processes that convert Tm values into barcodes according to a preferred embodiment of the present invention.

FIG. 11 shows examples of temperature-dependent melting curve graphs of each sample, obtained in Example 2. The first tube (set 1) contained PNA probes represented by SEQ ID NOs: 1 to 3, and the second tube (set 2) contained PNA probes represented by SEQ ID NOs: 4 to 6. Thus, for each sample, two figures were indicated as set 1 and set 2, respectively. The melting temperature on melting curve of each PNA probe was summarized for each sample (FIG. 15). It could be seen that melting curves obtained using the PNA probes according to the present invention had different melting temperatures (Tm) for SNPs of the samples. In FIG. 15, values with mutation were indicated by red color. In the case of P0-355, mutation sites were designed as a perfect match, suggesting that samples containing mutated subjects show high temperature values.

In order to confirm whether the reason why the melting temperature did differ among the samples would be because of a difference in the nucleotide sequence, the melting temperature was comparatively analyzed with the nucleotide sequences (FIGS. 16 and 17). In FIGS. 16 and 17, blue indicates major mutation positions, and red indicates nucleotides different from those in the PNA probes. It could be seen that a difference in the Tm value was attributable to a difference in the nucleotide sequence. It could be seen that there was a difference in Tm value among mutations. Based on this difference in the melting temperature, nucleotide sequence mutations can be detected. This result is consistent with one intended when the PNA nucleotide sequences according to the present invention were constructed. It could be seen that when several samples have the same nucleotide sequence, they showed the same Tm. This suggests that when samples show the same Tm, they have the same nucleotide sequence.

Example 4: Method of Detecting VHSV NV Gene Mutation Based on Melting Temperature Based on the results of Examples 2 and 3, a judgment table enabling the detection of NV gene mutations in actual VHSV samples can be made. Using the table, the detection of NV gene mutations is possible.

Figure 13:
FIG. 13 shows a series of processes that detect nucleotide sequence mutations based on barcodes according to a preferred embodiment of the present invention.

Based on the experimental results obtained as described above, two judgment criteria can be made: a judgment criterion for converting the Tm values shown in FIG. 12 into barcodes; and a judgment criterion for detecting nucleotide sequence mutations based on the barcodes shown in FIG. 13.

Figure 14:
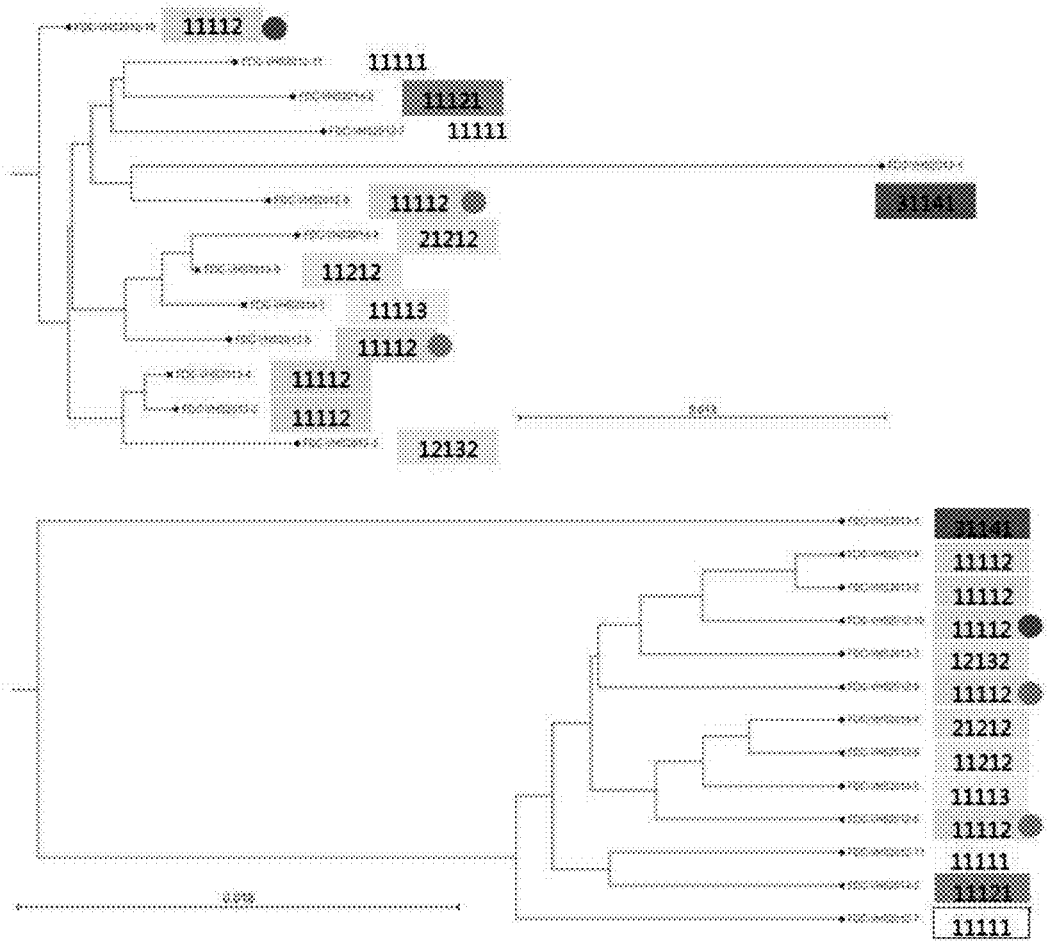
FIG. 14 shows a phylogenetic tree of VHSV mutations, obtained using barcodes created according to an example of the present invention.

Using the judgment criterion shown in FIG. 12, the Tm values of samples were converted into barcodes (FIG. 18). Using the judgment criterion shown in FIG. 13, nucleotide sequence mutations can be detected using the barcodes that imply the results (FIG. 19). In addition, FIG. 14 shows a phylogenetic tree of virus mutations detected in samples by use of the barcodes.

As described above, Tm values resulting from the real-time PCR results can be converted into barcodes for the PNA probes, and the results indicated by the barcodes can be expressed as nucleotide sequences through barcode criteria. Through such a series of processes, the PNA probes can rapidly detect mutations in the VHSV NV gene.

INDUSTRIAL APPLICABILITY

As described above, the present invention enables amplification and melting curves to be exhibited using a primer and a peptide nucleotide acid specific to the NV gene of viral hemorrhagic septicemia virus (VHSV), which is a virus causing infectious aquatic organism disease so that a mutation in a virus that causes infectious disease in aquatic organisms can be detected in a simple, rapid and accurate manner, infection of fish with the virus can be detected, and a mutation in the NV gene can be detected.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

The invention claimed is:

1. A method of determining a mutation in viral hemorrhagic septicemia virus (VHSV) non-viron (NV) gene by use of PNA probe(s) having attached thereto a reporter and a quencher, the method comprising the steps of:

(a) hybridizing each PNA probe to a sample by mixing (i) a sample containing either viral hemorrhagic septicemia virus (VHSV) or a target nucleic acid comprising a mutation site of the viral hemorrhagic septicemia virus (VHSV) non-viron (NV) gene, and (ii) a PNA probe that binds complementarily to the nucleotide sequence of the target nucleic acid comprising the mutation site of the viral hemorrhagic septicemia virus (VHSV) NV gene;

(b) obtaining melting temperatures of the hybridization products while changing the temperature of the hybridization products;

(c) sectionalizing each melting temperatures of the hybridization products as temperature zones for each PNA probes and assigning a code to the temperature zone; and (d) reacting a sample expected to have mutation under the same conditions as steps (a) to (b) to thereby obtain the melting temperature of the sample, and encoding the obtained melting temperature according to the assigned code of step (c), thereby determining the type of the mutation in viral hemorrhagic septicemia virus (VHSV) non-viron (NV) gene, wherein the PNA probe has a sequence represented by any one of SEQ ID NOs: 1 to 6.

2. The method of claim 1, wherein the code assigned to the melting temperature between a wild-type of the target nucleic acid and the PNA probe is different from a code assigned to the melting temperature between a mutant of the target nucleic acid and the PNA probe.

3. The method of claim 1, wherein the reporter is one or more selected from the group consisting of FAM (6-carboxyfluorescein), Texas red, HEX (2',4',5',7'-tetrachloro-6-carboxy-4,7-dichlorofluorescein), and Cy5.

4. The method of claim 1, wherein the quencher is one or more selected from the group consisting of TAMRA (6-carboxytetramethyl-rhodamine), BHQ1, BHQ2 and Dabcyl.

5. The method of claim 1, wherein the PNA probe is either a PNA probe set represented by SEQ ID NOs: 1 to 3 or a PNA probe set represented by SEQ ID NOs: 4 to 6.

6. A kit for confirming the position of a nucleotide sequence mutation in viral hemorrhagic septicemia virus (VHSV) non-viron (NV) gene, the kit comprising a plurality of PNA probes, each of which has a reporter and or a quencher attached thereto, binds complementarily to the viral hemorrhagic septicemia virus (VHSV) non-viron (NV) gene, and has the nucleotide sequence selected from the group consisting of SEQ ID NOs: 1 to 6.

7. The kit of claim 6, wherein the PNA probe is either a PNA probe set represented by SEQ ID NOs: 1 to 3 or a PNA probe set represented by SEQ ID NOs: 4 to 6.

* * * * *

UNITED STATES PATENT AND TRADEMARK OFFICE
CERTIFICATE OF CORRECTION

PATENT NO. : 11,473,154 B2
APPLICATION NO. : 15/777659
DATED : October 18, 2022
INVENTOR(S) : Jee Youn Hwang et al.

It is certified that error appears in the above-identified patent and that said Letters Patent is hereby corrected as shown below:

In the Specification

Column 14, Line 16, "2XqPCR" should be -- 2X qPCR --.

Column 14, Line 19, "(2.5 μmol)" should be -- (2.5 pmol) --.

Column 14, Line 20, "20XSSB" should be -- 20X SSB --.

Column 15, Line 15, "P0-355" should be -- PO-355 --.

Signed and Sealed this
Twentieth Day of December, 2022

Katherine Kelly Vidal
*Director of the United States Patent and Trademark Office*